(12) United States Patent
Zhang et al.

(10) Patent No.: US 9,890,149 B2
(45) Date of Patent: *Feb. 13, 2018

(54) ISOTHIAZOLE DERIVATIVES AS CFTR MODULATORS

(71) Applicant: NuBridge BioSciences, San Diego, CA (US)

(72) Inventors: Lin Zhang, San Diego, CA (US); Yu Ge, Shanghai (CN)

(73) Assignee: NuBridge BioSciences, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/287,686

(22) Filed: Oct. 6, 2016

(65) Prior Publication Data

US 2017/0101403 A1    Apr. 13, 2017

Related U.S. Application Data

(60) Provisional application No. 62/238,437, filed on Oct. 7, 2015.

(51) Int. Cl.
*C07D 417/14* (2006.01)
*C07D 417/12* (2006.01)

(52) U.S. Cl.
CPC ......... *C07D 417/14* (2013.01); *C07D 417/12* (2013.01)

(58) Field of Classification Search
CPC .................................................. C07D 417/14
USPC ...................................................... 546/271.1
See application file for complete search history.

(56) References Cited

U.S. PATENT DOCUMENTS

| 8,969,584 B2 * | 3/2015 | Ge | C07D 417/12 548/214 |
| 9,090,594 B2 * | 7/2015 | Ge | C07D 417/12 |
| 9,458,151 B2 * | 10/2016 | Ge | C07D 417/12 |

FOREIGN PATENT DOCUMENTS

CN          105254624     *    1/2016

OTHER PUBLICATIONS

King, Med. Chem., Principle and Practice (1994), pp. 206-208.*
U.S. Appl. No. 15/287,473, filed Oct. 6, 2016, Zhang, Lin.
U.S. Appl. No. 15/287,542, filed Oct. 6, 2016, Zhang, Lin.
Zielenski, J., Genotype and phenotype in cystic fibrosis, *Respiration*, 2000, 67(2), 117-133.
Sosnay, P.R. et al., Defining the disease liability of variants in the cystic fibrosis transmembrane conductance regulator gene, *Nat. Genet*. 2013, 45(10), 1160-1167.
Cystic Fibrosis Foundation. CFF Patient Registry, Bethesda, Maryland, 2014.
Knowles, M.R. et al., Mucus clearance as a primary innate defense mechanism for mammalian airways, *J. Clin. Invest.*, 2002, 109, 571-577.
Bronstein, M.N., Pancreatic insufficiency, growth, and nutrition in infants identified by newborn screening as having cystic fibrosis, *J. Pediatr*. 1992, 120, 533-540.
Dray, X. et al., Distal Intestinal Obstruction Syndrome in Adults With Cystic Fibrosis, *Clin. Gastroenterol. Hepatol.*,2004, 2, 498-503.
De Boeck, K., et al., Pancreatitis among patients with cystic fibrosis: correlation with pancreatic status and genotype, *Pediatrics*, 2005, 115, e463-e469.
Wang, X., et al., Mutation in the Gene Responsible for Cystic Fibrosis and Predisposition to Chronic Rhinosinusitis in the General Population, *JAMA.*, 2000, 284(14),1814-1819.
Quinton, P.M., Cystic Fibrosis: Lessons from the Sweat Gland, *Physiology*, 2007, 22, 212-225.
O'Sullivan, B.P. et al., Cystic fibrosis. *Lancet*. 2009, 373, 1891-1904.
Hirsh, A.J. et al., Evaluation of Second Generation Amiloride Analogs as Therapy for Cystic Fibrosis Lung Disease, *J. Pharmacol. Exp. Ther*., 2004, 311(3), 929-938.
Moody, C., et al., Inositol polyphosphate derivative inhibits Na transport and improves fluid dynamics in cystic fibrosis airway epithelia, *Am. J. Physiol. Cell Physiol.*, 2005, 289(3), C512-C520.
Pedemonte N., et al., Antihypertensive 1,4-dihydropyridines as correctors of the cystic fibrosis transmembrane conductance regulator channel gating defect caused by cystic fibrosis mutations, *Mol. Pharmacol.*, 2005, 68, 1736-1746.
Cystic Fibrosis Canada, Sexuality, Fertility and Cystic Fibrosis for Adults, website at cysticfibrosis.ca.

* cited by examiner

*Primary Examiner* — Taofiq A Solola
(74) *Attorney, Agent, or Firm* — Mei & Mark LLP; Manni Li

(57) ABSTRACT

A compound having the structure of Formula II, or a stereoisomer, tautomer, or a pharmaceutically acceptable salt thereof:

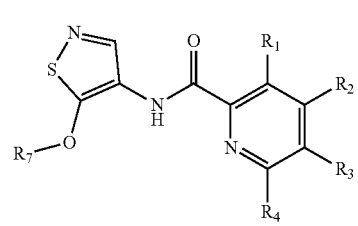

II

The compound is useful as CFTR modulator. Further, a method of using the compound and pharmaceutical composition comprising the compound are provided for treating diseases in lungs, pancreas, gastrointestinal system, sinuses, reproductive system, and the sweat glands.

15 Claims, No Drawings

ISOTHIAZOLE DERIVATIVES AS CFTR MODULATORS

CROSS-REFERENCE AND RELATED APPLICATION

The subject application claims priority on U.S. Provisional Application No. 62/238,437 filed on Oct. 7, 2015. The priority application is incorporated herein by reference.

TECHNICAL FIELD

The present invention relates to isothiazole derivatives, their preparation, and their pharmaceutical application in treating diseases. Particularly, isothiazole derivatives that are modulators of CFTR activities and useful for the treatment of inflammatory or obstructive airways diseases or mucosal hydration, including but not limited, cystic fibrosis.

BACKGROUND

Cystic Fibrosis Transmembrane Conductance Regulator (CFTR) is a protein kinase A (PKA) activated epithelial anion channel. It's responsible for transportation of salt and fluid in many organs through the apical membrane of epithelial cells. CFTR regulates fluid and electrolyte balance in epithelial tissues, such as in the lungs, sinuses, pancreas, intestine, reproductive system, and sweat glands (Zielenski, J., Genotype and phenotype in cystic fibrosis, *Respiration*, 2000, 67(2), 117-133).

Over 2000 mutations in the CFTR gene have been identified and the majority are extremely rare (Sosnay, P. R. et al., Defining the disease liability of variants in the cystic fibrosis transmembrane conductance regulator gene, *Nat. Genet.* 2013, 45(10), 1160-1167). ΔF508 is the most common CFTR mutation worldwide. Up to 91% of patients with CF have the ΔF508 mutation on at least one allele. There are 11 mutations occur at a frequency of >1% globally: G542X, G551D, R117H, N1303K, W1282X, R553X, 621+1G→T, 1717-1G→A, 3849+10kbC→T, 2789+5G→A, and 3120+1G→A. The mutations in the CFTR gene can cause disruptions at various stages of CFTR protein synthesis or in several aspects of CFTR protein function. They can result in less CFTR protein at the cell surface, virtual absence of CFTR protein, or dysfunctional CFTR protein at the cell surface (Zielenski, J., Genotype and phenotype in cystic fibrosis. *Respiration*, 2000, 67(2), 117-133).

Cystic fibrosis (CF), a systemic, multiorgan disease, is caused by loss of CFTR protein-mediated ion transport. Defective ion transport leads to an imbalance of fluid and electrolytes causing thick, sticky mucus and viscous secretions to accumulate in different organs; the defection interferes with the proper function of organs and causes diseases in lungs (such as cough, viscous sputum, dyspnea, chronic endobronchial infections and inflammation, bronchiectasis, and end-stage lung disease) (Cystic Fibrosis Foundation. CFF Patient Registry, Bethesda, Md., 2014; Knowles, M. R. et al., Mucus clearance as a primary innate defense mechanism for mammalian airways, *J. Clin. Invest.*, 2002, 109, 571-577), pancreas (such as pancreatic insufficiency, nutrient and fat malabsorption, vitamin deficiency, acute/chronic pancreatitis, and CF-related diabetes mellitus) (Bronstein, M. N., Pancreatic insufficiency, growth, and nutrition in infants identified by newborn screening as having cystic fibrosis, *J. Pediatr.* 1992, 120, 533-540), gastrointestinal system (gastroesophageal reflux disease, distal intestinal obstructive syndrome, biliary duct obstruction, focal biliary cirrhosis, and chronic constipation) (Dray, X. et al., Distal Intestinal Obstruction Syndrome in Adults With Cystic Fibrosis, *Clin. Gastroenterol. Hepatol.*, 2004, 2, 498-503; De Boeck, K., et al., Pancreatitis among patients with cystic fibrosis: correlation with pancreatic status and genotype, *Pediatrics*, 2005, 115, e463-e469), sinus (nasal congestion loss of smell, sinusitis, chronic infection, and nasal polyps) (Wang, X., et al., Mutation in the Gene Responsible for Cystic Fibrosis and Predisposition to Chronic Rhinosinusitis in the General Population, *JAMA.*, 2000, 284(14), 1814-1819), reproductive system (infertility and congenital bilateral absence of vas deferens) (Cystic Fibrosis Canada, Sexuality, Fertility and Cystic Fibrosis for Adults), and the sweat glands (such as excessive salt loss, dehydration, chronic metabolic alkalosis, heat prostration, and high levels of sweat chloride) (Quinton, P. M., Cystic Fibrosis: Lessons from the Sweat Gland, *Physiology*, 2007, 22, 212-225). Symptoms of CF manifest throughout life with great variability among patients, though lung disease is the primary cause of mortality (O'Sullivan, B. P. et al., Cystic fibrosis. *Lancet.* 2009, 373, 1891-1904). As a result, compounds that can modulate the CFTR activities and restore or enhance the function of mutant and wild type CFTR may be used to treat the above diseases.

The effect of modulating CFTR activities on inflammatory or obstructive airways diseases or mucosal hydration may be measured by determining the chloride ions' movement in cell-based assays (Hirsh, A. J. et al., Evaluation of Second Generation Amiloride Analogs as Therapy for Cystic Fibrosis Lung Disease, *J. Pharmacol. Exp. Ther.*, 2004, 311(3), 929-938; Moody, C., et al., Inositol polyphosphate derivative inhibits Na transport and improves fluid dynamics in cystic fibrosis airway epithelia, *Am. J. Physiol. Cell Physiol.*, 2005, 289(3), C512-0520).

SUMMARY OF THE INVENTION

The present invention provides a compound having a structure of Formula II, or a stereoisomer, a tautomer, or a pharmaceutically acceptable salt thereof:

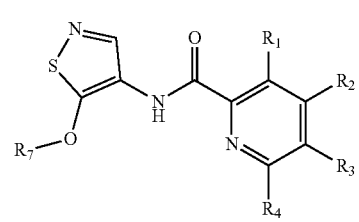

II wherein $R_1$ is a hydrogen (H), —$NHR_5$, a halogen, a hydroxyl, an alkyl, a cyano, or a nitro group; $R_2$ is a hydrogen, —$NHR_6$, a halogen, a hydroxyl, a substituted or substituted alkyl, an alkenyl, an alkynyl, an alkoxyl, a cycloalkyl, an amino, a cyano, or a nitro group; $R_3$ is a hydrogen, —$NHR_6$, a halogen, a hydroxyl, a halogenated alkyl, a substituted or unsubstituted alkyl, alkenyl, alkynyl, alkoxyl, or cycloalkyl, an amino, a cyano, or a nitro group; $R_4$ is a substituted or unsubstituted alkyl, alkenyl, alkynyl, alkoxyl, aryl, heteroaryl, cycloalkyl, or heterocyclyl, an alkyl amino, substituents on the substituted $R_4$ group are selected from a halogen, a cyano, an amino, a $C_{1-4}$ alkylamine, a $C_{1-4}$ alkyl, a $C_{3-6}$ cycloalkyl, an alkoxyl, a nitro, a carboxy, a carbonyl, a carboalkoxy, or an aminocarboxy; $R_5$ is a hydrogen, —C(=O)—$R_6$, a substituted or unsubstituted alkyl, cycloalkyl, heterocyclyl, aryl, or heteroaryl; $R_6$ is a substituted or unsubstituted alkyl, alkenyl, alkynyl, alkoxyl, or cycloalkyl, an amino, or a substituted amino group; Z is an $OR_S$, a $SR_S$, or a $SO_2R_7$; $R_7$ is an optionally substituted $C_{1-8}$ hydrocarbon group, or a group described in the following formula:

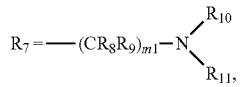

or a group described in the following formula:

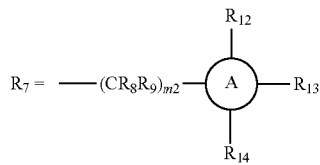

Each of $R_8$, $R_9$, $R_{10}$, $R_{11}$ is independently selected from a hydrogen, a halogenated $C_{1-8}$ alkyl, a hydroxyl substituted $C_{1-8}$ alkyl, a substituted or unsubstituted $C_{1-8}$ hydrocarbon group, and each of $R_{12}$, $R_{13}$, $R_{14}$ is independently selected from a hydrogen, a halogen, an $OR_{15}$, an $NR_{16}R_{17}$, a $C(=O)NR_{18}R_{19}$, or an optionally substituted $C_1$-$C_8$ hydrocarbon group; or $R_{12}$, $R_{13}$ and $R_{14}$, together with the atoms to which they are attached, may be joined together to form a chain so that the ring to which they are attached is a substituted $C_6$-$C_{14}$ membered spiral ring, a bicyclic ring, or a fused ring group; m1 is 2, 3, 4, or 5, and m2 is 0, 1, or 2, and Ring A is a 4-8 member substituted or unsubstituted aryl, heteroaryl, *cycloalkyl*, cycloalkenyl, or a heterocyclyl containing 1 or 2 hetero atoms that are independently selected from an oxygen, a nitrogen or a sulfur;

Each of $R_{15}$, $R_{16}$, $R_{17}$, $R_{18}$, $R_{19}$, is independently selected from a hydrogen (H) or an optionally substituted $C_1$-$C_8$ hydrocarbon group;

$R_{20}$ is an H, an optionally substituted hydrocarbon group, an optionally substituted cyclic hydrocarbon group, an optionally substituted heterocyclyl group, a $C(=O)R_{22}$, a $C(=O)OR_{22}$, or a $C(=O)NHR_{22}$;

$R_{21}$ is an OH, an $NHR_{22}$, a $C(=O)OR_{22}$, or a $C(=O)NHR_{22}$; and $R_{22}$ is an H or an optionally substituted $C_{1-8}$ hydrocarbon group.

The present invention further provides a CFTR modulator that is 6-(2,6-difluorophenyl)-5-fluoro-N-(5-(piperidin-4-ylmethoxy)isothiazol-4-yl)picolinamide hydrochloride, N-(5-(azetidin-3-ylmethoxy)isothiazol-4-yl)-6-(2,6-difluorophenyl)-5-fluoropicolinamide hydrochloride, 6-(2,6-difluorophenyl)-5-fluoro-N-(5-(piperidin-4-yloxy)isothiazol-4-yl)picolinamide hydrochloride, 6-(2,6-difluorophenyl)-5-fluoro-N-(5-(pyrrolidin-3-yloxy)isothiazol-4-yl)picolinamide hydrochloride, 6-(2,6-difluorophenyl)-5-fluoro-N-(5-(piperidin-3-yloxy)isothiazol-4-yl)picolinamide hydrochloride, N-(5-(azepan-4-yloxy)isothiazol-4-yl)-6-(2,6-difluorophenyl)-5-fluoropicolinamide hydrochloride, 6-(2,6-difluorophenyl)-5-fluoro-N-(5-(piperidin-3-ylmethoxy)isothiazol-4-yl) picolinamide hydrochloride, 6-(2,6-difluorophenyl)-5-fluoro-N-(5-(pyrrolidin-3-ylmethoxy)isothiazol-4-yl) picolinamide hydrochloride, N-(5-(azetidin-3-yloxy) isothiazol-4-yl)-6-(2,6-difluorophenyl)-5-fluoropicolinamide hydrochloride, N-(5-(((1r,4r)-4-aminocyclohexyl)oxy)isothiazol-4-yl)-6-(2,6-difluorophenyl)-5-fluoropicolinamide hydrochloride, N-(5-((3-aminocyclohexyl)oxy) isothiazol-4-yl)-6-(2,6-difluorophenyl)-5-fluoropicolinamide hydrochloride, N-(5-(3-aminopropoxy)isothiazol-4-yl)-6-(2,6-difluorophenyl)-5-fluoropicolinamide hydrochloride, 6-(2,6-difluorophenyl)-5-fluoro-N-(5-(3-(methylamino)propoxy)isothiazol-4-yl) picolinamide hydrochloride, 6-(2,6-difluorophenyl)-N-(5-(3-(dimethylamino)propoxy)isothiazol-4-yl)-5-fluoropicolinamide hydrochloride, N-(5-(4-aminobutoxy) isothiazol-4-yl)-6-(2,6-difluorophenyl)-5-fluoropicolinamide hydrochloride, 6-(2,6-difluorophenyl)-5-fluoro-N-(5-(4-(methylamino)butoxy)isothiazol-4-yl) picolinamide hydrochloride, 6-(2,6-difluorophenyl)-5-fluoro-N-(5-(3-hydroxypropoxy)isothiazol-4-yl) picolinamide, 6-(2,6-difluorophenyl)-5-fluoro-N-(5-(3-hydroxybutoxy)isothiazol-4-yl)picolinamide, 6-(2,6-difluorophenyl)-5-fluoro-N-(5-(4-hydroxybutoxy) isothiazol-4-yl)picolinamide, 6-(2,6-difluorophenyl)-5-fluoro-N-(5-((4-hydroxy-4-methylpentyl)oxy)isothiazol-4-yl)picolinamide, 6-(2,6-difluorophenyl)-N-(5-(3,4-dihydroxybutoxy)isothiazol-4-yl)-5-fluoropicolinamide, 6-(2,6-difluorophenyl)-5-fluoro-N-(5-((tetrahydro-2H-pyran-4-yl)methoxy)isothiazol-4-yl)picolinamide, 3-amino-6-(2,6-difluorophenyl)-5-fluoro-N-(5-(piperidin-4-ylmethoxy)isothiazol-4-yl)picolinamide hydrochloride, 3-amino-6-(2,6-difluorophenyl)-5-fluoro-N-(5-(pyrrolidin-3-yloxy)isothiazol-4-yl)picolinamide hydrochloride, 3-amino-6-(2,6-difluorophenyl)-5-fluoro-N-(5-(piperidin-4-yloxy)isothiazol-4-yl)picolinamide hydrochloride, 3-amino-N-(5-(azepan-4-yloxy)isothiazol-4-yl)-6-(2,6-difluorophenyl)-5-fluoropicolinamide hydrochloride, 3-amino-N-(5-(((1r,4r)-4-aminocyclohexyl)oxy)isothiazol-4-yl)-6-(2,6-difluorophenyl)-5-fluoropicolinamide hydrochloride, 3-amino-6-(2,6-difluorophenyl)-5-fluoro-N-(5-(pyrrolidin-3-ylmethoxy)isothiazol-4-yl)picolinamide hydrochloride, N-(5-((1-amino-3-chloropropan-2-yl)oxy)isothiazol-4-yl)-6-(2,6-difluorophenyl)-5-fluoropicolinamide hydrochloride, N-(5-(3-amino-2-(chloromethyl)propoxy)isothiazol-4-yl)-6-(2,6-difluorophenyl)-5-fluoropicolinamide hydrochloride, 3-amino-N-(5-(azetidin-3-yloxy)isothiazol-4-yl)-6-(2,6-difluorophenyl)-5-fluoropicolinamide hydrochloride, 3-amino-N-(5-(azetidin-3-ylmethoxy)isothiazol-4-yl)-6-(2,6-difluorophenyl)-5-fluoropicolinamide hydrochloride, 3-amino-N-(5-((1-amino-3-chloropropan-2-yl)oxy)isothiazol-4-yl)-6-(2,6-difluorophenyl)-5-fluoropicolinamide hydrochloride, 3-amino-N-(5-(3-amino-2-(chloromethyl)propoxy)isothiazol-4-yl)-6-(2,6-difluorophenyl)-5-fluoropicolinamide hydrochloride, 3-amino-6-(2,6-difluorophenyl)-5-fluoro-N-(5-(piperidin-3-ylmethoxy)isothiazol-4-yl)picolinamide hydrochloride, 3-amino-N-(5-(4-aminobutoxy)isothiazol-4-yl)-6-(2,6-difluorophenyl)-5-fluoropicolinamide hydrochloride, 3-amino-N-(5-((3-aminocyclohexyl)oxy)isothiazol-4-yl)-6-(2,6-difluorophenyl)-5-fluoropicolinamide hydrochloride, 3-amino-5-fluoro-6-phenyl-N-(5-(pyrrolidin-3-yloxy)isothiazol-4-yl)picolinamide hydrochloride, 3-fluoro-N-(5-(piperidin-4-yloxy)isothiazol-4-yl)-[2,4'-bipyridine]-6-carboxamide hydrochloride, N-(5-(azepan-4-yloxy)isothiazol-4-yl)-6-(2,6-difluorophenyl)-3-fluoropicolinamide hydrochloride, N-(5-(azepan-4-yloxy)isothiazol-4-yl)-5-fluoro-6-(2-fluoro-6-methoxyphenyl)picolinamide hydrochloride, N-(5-(azepan-4-yloxy)isothiazol-4-yl)-6-(2,6-difluorophenyl)-5-(trifluoromethyl)picolinamide hydrochloride, 6-(2,6-difluorophenyl)-N-(5-(piperidin-4-ylmethoxy)isothiazol-4-yl)-5-(trifluoromethyl)picolinamide hydrochloride, N-(5-(azetidin-3-ylmethoxy)isothiazol-4-yl)-6-(2,6-difluorophenyl)-5-(trifluoromethyl)picolinamide hydrochloride, 6-(2,6-difluorophenyl)-N-(5-(piperidin-4-yloxy)isothiazol-4-yl)-5-(trifluoromethyl)picolinamide hydrochloride, N-(5-(((1r,4r)-4-aminocyclohexyl)oxy)isothiazol-4-yl)-6-(2,6-difluorophenyl)-5-(trifluoromethyl)picolinamide hydrochloride, 6-(2,6-difluorophenyl)-N-(5-((tetrahydro-2H-pyran-4-yl)methoxy)isothiazol-4-yl)-5-(trifluoromethyl)picolinamide, 3-amino-N-(5-(azepan-4-yloxy)isothiazol-4-yl)-6-(2,6-difluorophenyl)-5-(trifluoromethyl)picolinamide hydrochloride, 3-amino-6-(2,6-difluorophenyl)-N-(5-(piperidin-4-ylmethoxy)isothiazol-4-yl)-5-(trifluoromethyl)picolinamide hydrochloride, 3-amino-N-(5-(azetidin-3-ylmethoxy)isothiazol-4-yl)-6-(2,6-difluorophenyl)-5-(trifluoromethyl)picolinamide hydrochloride, 3-amino-6-(2,6-difluorophenyl)-N-(5-(piperidin-4-yloxy)isothiazol-4-yl)-5-(trifluoromethyl)picolinamide hydrochloride, 3-amino-N-(5-(((1r,4r)-4-aminocyclohexyl)oxy)isothiazol-4-yl)-6-(2,6-difluorophenyl)-5-(trifluoromethyl)picolinamide hydrochloride, 3-amino-6-phenyl-N-(5-(pyrrolidin-3-yloxy)isothiazol-4-yl)-5-(trifluoromethyl)picolinamide hydrochloride, N-(5-(3-amino-2-(chloromethyl)propoxy)isothiazol-4-yl)-6-(2,6-difluorophenyl)-5-(trifluoromethyl)picolinamide hydrochloride, 3-amino-N-(5-(3-amino-2-(chloromethyl)propoxy)isothiazol-4-yl)-6-(2,6-difluorophenyl)-5-(trifluoromethyl)picolinamide hydrochloride, N-(5-(3-amino-2-(hydroxymethyl)propoxy)isothiazol-4-yl)-6-(2,6-difluorophenyl)-5-fluoropicolinamide hydrochloride, 3-amino-N-(5-(3-amino-2-(hydroxymethyl)propoxy)isothiazol-4-yl)-6-(2,6-difluorophenyl)-5-fluoropicolinamide hydrochloride, N-(5-(3-amino-2-(hydroxymethyl)propoxy)isothiazol-4-yl)-6-(2,6-difluorophenyl)-5-(trifluoromethyl)picolinamide hydrochloride, 3-amino-N-(5-(3-amino-2-(hydroxymethyl)propoxy)isothiazol-4-yl)-6-(2,6-difluorophenyl)-5-(trifluoromethyl)picolinamide hydrochloride, N-(5-((3-aminocyclohexyl)oxy)isothiazol-4-yl)-6-(2,6-difluorophenyl)-5-(trifluoromethyl)picolinamide hydrochloride, or 3-amino-N-(5-((3-aminocyclohexyl)oxy)isothiazol-4-yl)-6-(2,6-difluorophenyl)-5-(trifluoromethyl)picolinamide hydrochloride.

The present invention further provides a method for using the compound, comprising administering to a subject in need of a treatment a therapeutically effective amount of the compound of the present invention. The treatment is for treating diseases in lungs, pancreas, gastrointestinal system, sinuses, reproductive system, and the sweat glands.

The present invention further provides a pharmaceutical composition comprising the compound as an active pharmaceutical ingredient and pharmaceutically acceptable carriers and adjuvants. The pharmaceutical composition may further comprises antibiotics, antihistamines, anti-inflammatory agents, bronchodilatory agents, ENaC blockers, osmotic agents, or a combination thereof.

DETAILED DESCRIPTION OF THE INVENTION

The present invention provides isothiazole derivatives and their stereoisomers, tautomers, and pharmaceutically acceptable salts have the following general structural Formula I:

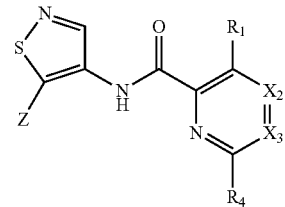

wherein $X_2$ and $X_3$ are independently selected from a $CR_2$, a $CR_3$, or a nitrogen (N), provided that $X_2$ and $X_3$ cannot be N at the same time;

$R_1$ is a hydrogen (H), —$NHR_5$, a halogen, a hydroxyl, an alkyl, a cyano, or a nitro group;

$R_2$ is selected from a hydrogen, —$NHR_6$, a halogen, a hydroxyl, a substituted or unsubstituted alkyl, an alkenyl, an alkynyl, an alkoxyl, a *cycloalkyl*, an amino, a cyano, or a nitro group;

$R_3$ is selected from a hydrogen, —$NHR_6$, a halogen, a hydroxyl, a halogenated alkyl, a substituted or unsubstituted alkyl, alkenyl, alkynyl, alkoxyl, or *cycloalkyl*, an amino, a cyano, and a nitro group;

$R_4$ is a substituted or unsubstituted alkyl, alkenyl, alkynyl, alkoxyl, aryl, heteroaryl, *cycloalkyl*, or heterocyclyl, an alkyl amino, substituents on the substituted $R_4$ group are selected from a halogen, a cyano, an amino, a $C_{1-4}$ alkylamine, a $C_{1-4}$ alkyl, a $C_{3-6}$ *cycloalkyl*, an alkoxyl, a nitro, a carboxy, a carbonyl, a carboalkoxy, or an aminocarboxy;

$R_5$ is a hydrogen, —C(=O)—$R_6$, a substituted or unsubstituted alkyl, *cycloalkyl*, heterocyclyl, aryl, or heteroaryl;

$R_6$ is a substituted or unsubstituted alkyl, alkenyl, alkynyl, alkoxyl, or *cycloalkyl*, an amino, or a substituted amino group;

Z is an $OR_7$, a $SR_7$, or a $SO_2R_7$;

$R_7$ is an optionally substituted $C_{1-8}$ hydrocarbon group, or a group described in the following formula:

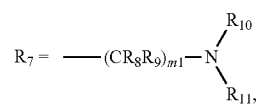

or a group described in the following formula:

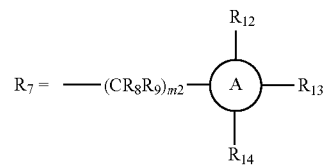

Wherein each of $R_8$, $R_9$, $R_{10}$, $R_{11}$ is independently selected from a hydrogen, a halogenated $C_{1-8}$ alkyl, a hydroxyl substituted $C_{1-8}$ alkyl, a substituted or unsubstituted $C_{1-8}$ hydrocarbon group, and each of $R_{12}$, $R_{13}$, $R_{14}$ is independently selected from a hydrogen, a halogen, an $OR_{15}$, a $NR_{16}R_{17}$, a C(=O)$NR_{18}R_{19}$, or an optionally substituted $C_1$-$C_8$ hydrocarbon group; or $R_{12}$, $R_{13}$ and $R_{14}$, together with the atoms to which they are attached, may be joined together to form a chain so that the ring to which they are attached is a substituted $C_6$-$C_{14}$ membered spiral ring, a bicyclic ring, or a fused ring group, and m1 is 2, 3, 4, or 5, and m2 is 0, 1, or 2, and Ring A is a 4-8 membered substituted or unsubstituted aryl, heteroaryl, *cycloalkyl*, cycloalkenyl, and heterocyclyl containing 1 or 2 hetero atoms that are independently selected from an oxygen, a nitrogen or a sulfur, and Each of $R_{15}$, $R_{16}$, $R_{17}$, $R_{18}$, $R_{19}$, is independently selected from a hydrogen (H) or an optionally substituted $C_1$-$C_8$ hydrocarbon group, and $R_{20}$ is an H, an optionally substituted hydrocarbon group, an optionally substituted cyclic hydrocarbon group, an optionally substituted heterocyclyl group, a C(=O)$R_{22}$, a C(=O)O$R_{22}$, or a C(=O)NH$R_{22}$, and $R_{21}$ is an OH, an NH$R_{22}$, a C(=O)O$R_{22}$, or a C(=O)NH$R_{22}$, and $R_{22}$ is an H or an optionally substituted $C_1$-$C_8$ hydrocarbon group.

In some embodiments of the present invention, the compounds of Formula I or a stereoisomer, tautomer, or pharmaceutically acceptable salt thereof have $X_2$ and $X_3$ that are $CR_2$ and $CR_3$, respectively.

The present invention further provides the compounds of Formula I and their stereoisomer, tautomer, or pharmaceutically acceptable salt thereof having the structure of formula I where $X_2$ is $CR_2$, $X_3$ is $CR_3$, and Z is O—$R_7$, and the structure is described as the following formula II:

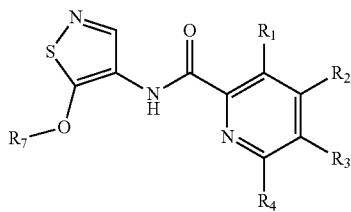

In the present invention, the compounds of Formula I or II, or a stereoisomer, tautomer, or pharmaceutically acceptable salt thereof are provided where $R_1$ may be a hydrogen, an amino, or a fluoro.

In the present invention, the compounds of Formula I or II, or a stereoisomer, tautomer, or pharmaceutically acceptable salt thereof are provided where $R_4$ may be a substituted or unsubstituted alkyl, alkenyl, or alkynyl. Substituents are independently selected from a halogen, a cyano, an amino, an alkyl amino, a cyclic amino, an alkyl, an alkoxy, a *cycloalkyl*, alkyl amino, a nitro, a carboxyl, a carboalkoxy, an aminocarboxy, a substituted aminocarbonyl, an aminosulfonyl, a substituted aminosulfonyl, or an alkoxyalkyl.

In the present invention, the compounds of Formula I or II, or a stereoisomer, tautomer, or pharmaceutically acceptable salt thereof are provided where $R_4$ may be a substituted or unsubstituted aryl, heteroaryl, $C_4$-$C_6$ *cycloalkyl*, or heterocyclyl, a partially unsaturated $C_4$-$C_6$ *cycloalkyl*, where each group may be substituted with up to four substituents that is a halogen, a cyano, an amino, an alkyl, an alkoxy, a *cycloalkyl*, a nitro, a carboxyl, a carboalkoxy, an aminocarboxy, a substituted aminocarbonyl, an aminosulfonyl, a substituted aminosulfonyl, or an alkoxyalkyl.

In the present invention, the compounds of Formula I or II, or a stereoisomer, tautomer, or pharmaceutically acceptable salt thereof are provided where $R_2$ may be a hydrogen, a methyl, an ethyl, a halogen, or a cyano group, $R_3$ is selected from a methyl, a $CF_3$, an ethyl, a $C_2F_5$, a halogen, or a cyano group.

As used herein, the term "substituent" refers to an atom or atomic group that replaces the hydrogen atoms of the molecule.

As used herein, "optionally substituted" substituent refers to substituents that each of the replaceable hydrogen atoms on the substituents may be substituted by other atom or atomic group.

As used herein, the term "hydrocarbon group" refers to an alkyl group (saturated aliphatic group), an alkenyl group (having at least one carbon-carbon double bond), an alkynyl group (having at least one carbon-carbon triple bond); the "hydrocarbon group" may be linear, branched, or cyclic; the "hydrocarbon group" may be aliphatic or aromatic.

As used herein, the term "cyclic hydrocarbon group" refers to a *cycloalkyl* group a cycloalkenyl group (having at least one carbon-carbon double bond), or an aromatic group; "cyclic hydrocarbon group" may be a monocyclic, bicyclic or multi-cyclic group; "cyclic hydrocarbon group" may be a spiral or fused ring.

As used herein, the term "hydrocarbon group" refers to an alkyl, an alkenyl, or an alkynyl group; "cyclic hydrocarbon group" refers to an aryl, a *cycloalkyl* group, or a cycloalkenyl group (having at least one carbon-carbon double bond); "heteroaryl" refers to an aromatic group with one or more ring atoms that are hetero atoms such as N, O, S, or a combination thereof; "heterocyclyl" and "cyclic hydrocarbon group" may be a monocyclic, bicyclic, or multi-cyclic group, and may be a spiral or fused ring.

As used herein, the term "substituent" includes but is not limited to a halogen (F, Cl, Br, I), —O$R_{23}$, —OC(=O) $R_{24}$, —OC(=O)N$R_{23}R_{24}$, =O, —S$R_{23}$, —SO$R_{23}$, —SO$_2R_{23}$, —SO$_2$N$R_{23}R_{24}$, —C(=O)$R_{23}$, —C(=O)O$R_{23}$, —C(=O)N$R_{23}R_{24}$, —$R_{23}$CN, —N$R_{23}R_{24}$, —NHC(=O)$R_{23}$, —NHC(=O)N$R_{23}R_{24}$, —NHC(=S)N$R_{23}R_{24}$, or a halogenated (F, Cl, Br, I) hydrocarbon; and each of $R_{23}$ and $R_{24}$ is independently selected from an H or an optionally substituted $C_1$-$C_8$ hydrocarbon group.

As used herein, the term "stereoisomers" includes any of the various stereoisomeric configurations that may exist for a given compound of the present invention, such as enantiomers, diastereomers, and geometric isomers. They can be pure chiral compounds, racemic mixtures, optically active compounds, pure diastereomers, or mixed diastereomers.

All the formulae given herein are intended to include both unlabeled and isotopically labeled form of the compound. Examples of the isotopes of hydrogen, carbon nitrogen, fluorine, and sulfur are $^2H$, $^3H$, $^{13}C$, $^{14}C$, $^{15}N$, $^{18}F$, and $^{35}S$, respectively.

The compounds described in the present invention that are acidic in nature can form pharmaceutically acceptable salts by reacting with physiologically compatible organic or inorganic bases, such as readily soluble alkali and alkaline earth salts, and salts formed from reacting with ammonia, N-methyl-glucamine, dimethyl-glucamine, ethyl-glucamine, lysine, ethanolamine, glucosamine, sarcosine, serine, tris(hydroxymethyl)aminomethane, or 1-amino-2,3,4-butanetriol.

The compounds described in the present invention that are basic in nature can form pharmaceutically acceptable salts by reacting with physiologically compatible organic or inorganic acids, such as the salts formed by reacting with hydrochloric acid, hydrobromic acid, sulfuric acid, phosphoric acid, methanesulfonic acid, toluene-sulfonic acid, carbonic acid, succinic acid, citric acid, benzoic acid, oxalic acid, malonic acid, salicylic acid, malic acid, fumaric acid, maleic acid, or acetic acid.

The present invention also provides the method for synthesizing the above CFTR modulators. The compounds in the present invention are made from commercially available starting materials and reagents. The present invention is illustrated in the following reaction scheme:

(1) The general procedure for the synthesis of compounds of Formula II:

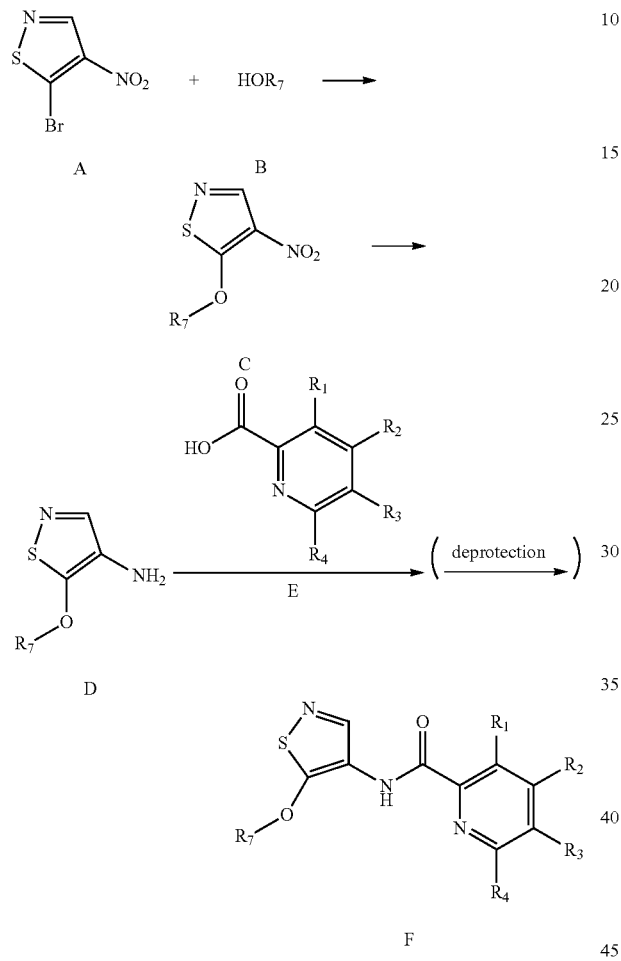

Alcohol B (1 eq.), protected or unprotected, reacts with a base, for example, NaH (1-3 eq.), in a solvent, for example, THF, at room temperature (25° C.) for 1 hour, then reacts with 5-bromo-4-nitroisothiazole A (1 eq.) at 25-50° C. for 1-10 hours to form nitroisothiazole ether C. C (1 eq.) is hydrogenated at 1-3 atm of hydrogen in the presence of 10% Pd/C (0.1-0.5 eq.) in a solvent such as 1:1 mixture of methanol and ethylacetate for 4-12 hours to get aminoisothiazole D. Protected or unprotected aromatic carboxylic acid E (1 eq.), in the presence of a coupling reagent, for example, HATU (1-1.5 eq.), a base, for example, DIEA (3 eq.), in a solvent, for example DMF, at heated conditions, for example 40° C., reacts with amine D (1 eq.) for 0.5-8 hours to form ether F. If there is no protecting group in E, then E is final ether product of Formula I or II. If F is protected by protecting group, for example, BOC or trimethylsilyl group, it's deprotected by treating with an acid such as trifluoroacetic acid (10-100 eq.) with equal volume of dichloromethane at room temperature (25° C.) for 1-16 hours. The final ether product F of Formula I or II is obtained after removing the solvent in vacuo at room temperature (25° C.).

The present invention also provides the pharmaceutical application of the above CFTR modulator. These isothiazole derivatives can be used to treat lung diseases (such as cough, viscous sputum, dyspnea, chronic endobronchial infections and inflammation, bronchiectasis, and end-stage lung disease), pancreatic diseases (such as pancreatic insufficiency, nutrient and fat malabsorption, vitamin deficiency, acute/chronic pancreatitis, and CF-related diabetes mellitus), gastrointestinal system diseases (gastroesophageal reflux disease, distal intestinal obstructive syndrome, biliary duct obstruction, focal biliary cirrhosis, and chronic constipation), sinus diseases (nasal congestion loss of smell, sinusitis, chronic infection, and nasal polyps), reproductive system diseases (infertility and congenital bilateral absence of vas deferens), and the sweat glands (such as excessive salt loss, dehydration, chronic metabolic alkalosis, heat prostration, and high levels of sweat chloride).

The compounds with formula (I) or (II) can be used in conjunction of other drugs or therapies, such as antibiotics, antihistamines, anti-inflammatory agents, bronchodilatory agents, ENaC blockers, or osmotic agents.

EXAMPLES

The following examples are set forth for illustration only to help understand the invention described herein and not to be construed as limiting the present invention in any manner.

Example 1

Synthesis of 6-(2,6-difluorophenyl)-5-fluoro-N-(5-(piperidin-4-ylmethoxy)isothiazol-4-yl)picolinamide hydrochloride (1)

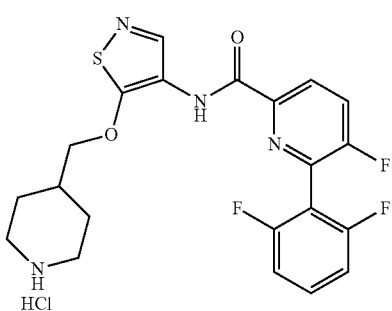

(1) Synthesis of tert-butyl 4-(((4-nitroisothiazol-5-yl)oxy)methyl)piperidine-1-carboxylate (C1)

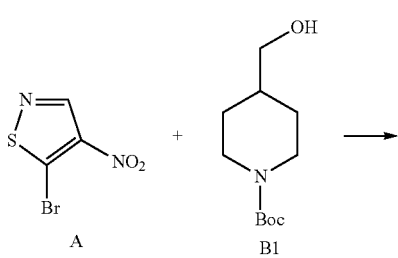

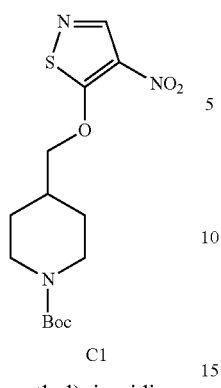

C1

To a solution of tert-butyl 4-(hydroxymethyl)piperidine-1-carboxylate (B1) (250 mg, 1.16 mmol) in THF (5 ml) at room temperature (25° C.) was added NaH (33 mg, 1.39 mmol) and stirred at room temperature for 20 minutes. 5-bromo-4-nitroisothiazole (A) (242 mg, 1.16 mmol) was added. The reaction mixture was stirred at 50° C. for 5 hours and the solvent was removed in vacuo. The residue was purified with flash chromatography eluded with 10-30% ethylacetate in petroleum ether to afford a the product C1 (247 mg, 0.719 mmol)

(2) tert-butyl 4-(((4-aminoisothiazol-5-yl)oxy)methyl)piperidine-1-carboxylate (D1)

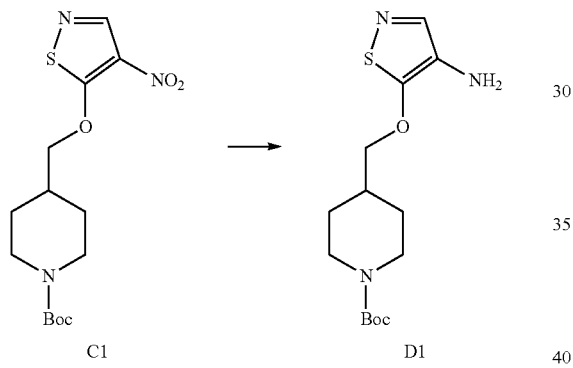

To a solution of C1 (200 mg, 0.582 mmol) in a mixed solvent of methanol (2 ml) and ethylacetate (2 ml) at room temperature (25° C.) was added 10% Pd/C. The mixture was stirred under hydrogen (1 atm) for 10 hours. The mixture was then filtered and the filtrate was concentrated to yield the product D1 (167 mg, 0.534 mmol)

(3) Synthesis of tert-butyl 4-(((4-(6-(2,6-difluorophenyl)-5-fluoropicolinamido)isothiazol-5-yl)oxy)methyl)piperidine-1-carboxylate (Boc-F1)

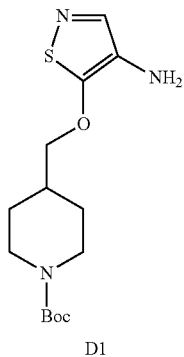

D1

+

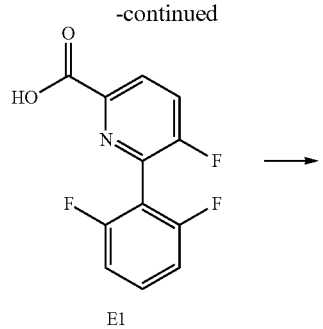

E1

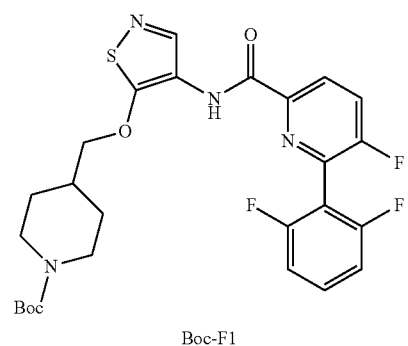

Boc-F1

Compound (D1) (50 mg, 0.16 mmol), 6-(2,6-difluorophenyl)-5-fluoropicolinic acid (E1) (40 mg, 0.16 mmol, HATU (72 mg, 0.19 mmol) and DIEA (88 μL, 0.507 mmol) are mixed in DMF (5 mL) and stirred at 50° C. for 1 hour. The reaction mixture was cooled to room temperature and diluted with ethyl acetate (50 mL), washed with brine, dried over $Na_2SO_4$, and concentrated in vacuo. The residue was purified with flash column (eluent: 10-30% ethyl acetate/petroleum ether) to obtain the product Boc-F1 (31 mg, 0.056 mmol).

(4) Synthesis of 6-(2,6-difluorophenyl)-5-fluoro-N-(5-(piperidin-4-ylmethoxy)isothiazol-4-yl)picolinamide hydrochloride (1)

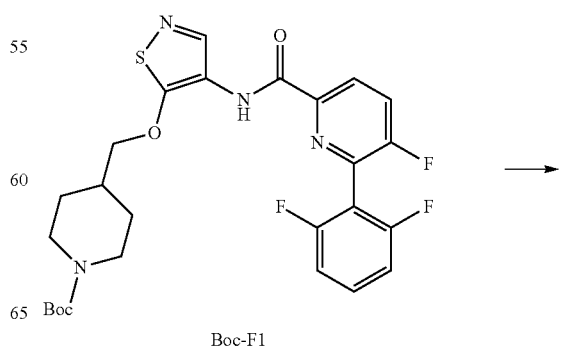

Boc-F1

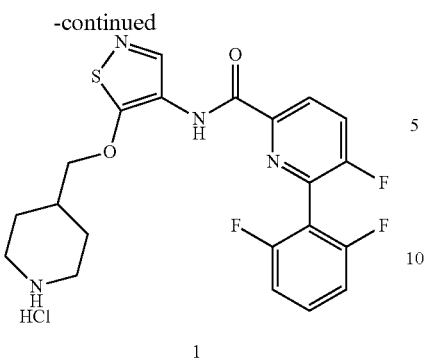

At room temperature, TFA (trifluoroacetic acid) (0.5 mL) was added to a solution of Compound Boc-F1 (20 mg, 0.036 mmol) in CH$_2$Cl$_2$ (1 mL) and stirred for 10 min. The mixture was the concentrated in vacuo. The residue was dissolved in CH$_2$Cl$_2$ (10 mL) and washed with NaOH (5 mL) and brine (5 mL), dried over Na$_2$SO$_4$, and concentrated in vacuo to obtain the title compound 1 (10 mg, 0.022 mmol).

Example 2

Synthesis of N-(5-(azetidin-3-ylmethoxy)isothiazol-4-yl)-6-(2,6-difluorophenyl)-5-fluoropicolinamide hydrochloride (2)

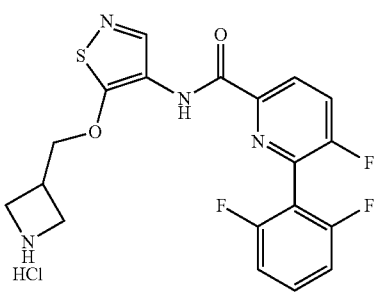

Following the procedure described in Example 1, and substituting compound B1 in Step (1) with tert-butyl 3-(hydroxymethyl)azetidine-1-carboxylate (B2), the title compound 2 was obtained.

Example 3

Synthesis of 6-(2,6-difluorophenyl)-5-fluoro-N-(5-(piperidin-4-yloxy)isothiazol-4-yl)picolinamide hydrochloride (3)

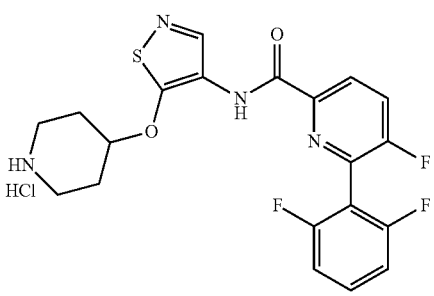

Following the procedure described in Example 1, and substituting compound B1 in Step (1) with tert-butyl 4-hydroxypiperidine-1-carboxylate (B3), the title compound 3 was obtained.

Example 4

Synthesis of 6-(2,6-difluorophenyl)-5-fluoro-N-(5-(pyrrolidin-3-yloxy)isothiazol-4-yl)picolinamide hydrochloride (4)

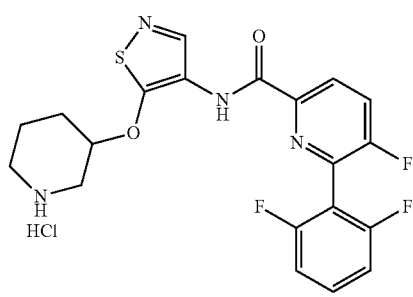

Following the procedure described in Example 1, and substituting Compound B1 in Step (1) with tert-butyl 3-hydroxypyrrolidine-1-carboxylate (B4), the title compound 4 was obtained.

Example 5

Synthesis of 6-(2,6-difluorophenyl)-5-fluoro-N-(5-(piperidin-3-yloxy)isothiazol-4-yl)picolinamide hydrochloride (5)

Following the procedure described in Example 1, and substituting Compound B1 in Step (1) with tert-butyl 3-hydroxypiperidine-1-carboxylate (B5), the title compound 5 was obtained.

Example 6

Synthesis of N-(5-(azepan-4-yloxy)isothiazol-4-yl)-6-(2,6-difluorophenyl)-5-fluoropicolinamide hydrochloride (6)

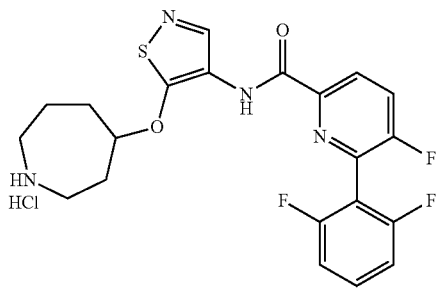

Following the procedure described in Example 1, and substituting Compound B1 in Step (1) with tert-butyl 4-hydroxyazepane-1-carboxylate (B6), the title compound 6 was obtained.

Example 7

Synthesis of 6-(2,6-difluorophenyl)-5-fluoro-N-(5-(piperidin-3-ylmethoxy)isothiazol-4-yl)picolinamide hydrochloride (7)

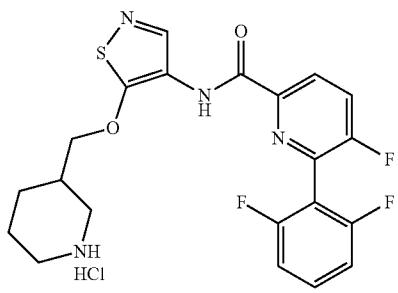

Following the procedure described in Example 1, and substituting Compound B1 in Step (1) with tert-butyl 3-(hydroxymethyl)piperidine-1-carboxylate (B7), the title compound 7 was obtained.

Example 8

Synthesis of 6-(2,6-difluorophenyl)-5-fluoro-N-(5-(pyrrolidin-3-ylmethoxy)isothiazol-4-yl)picolinamide hydrochloride (8)

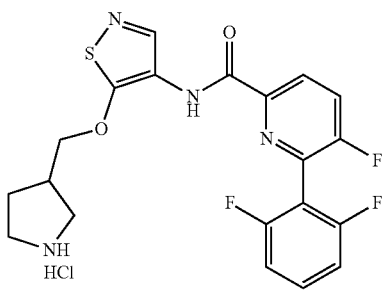

Following the procedure described in Example 1, and substituting Compound B1 in Step (1) with tert-butyl 3-(hydroxymethyl)pyrrolidine-1-carboxylate (B8), the title compound 8 was obtained.

Example 9

Synthesis of N-(5-(azetidin-3-yloxy)isothiazol-4-yl)-6-(2,6-difluorophenyl)-5-fluoropicolinamide hydrochloride (9)

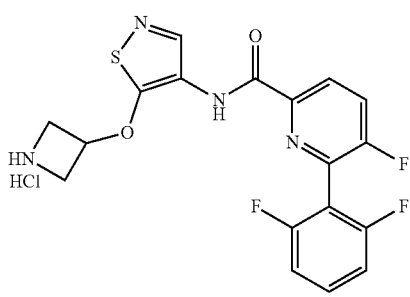

Following the procedure described in Example 1, and substituting Compound B1 in Step (1) with tert-butyl 3-(hydroxymethyl)azetidine-1-carboxylate (B9), the title compound 9 was obtained.

Example 10

Synthesis of N-(5-(((1r,4r)-4-aminocyclohexyl)oxy)isothiazol-4-yl)-6-(2,6-difluorophenyl)-5-fluoropicolinamide hydrochloride (10)

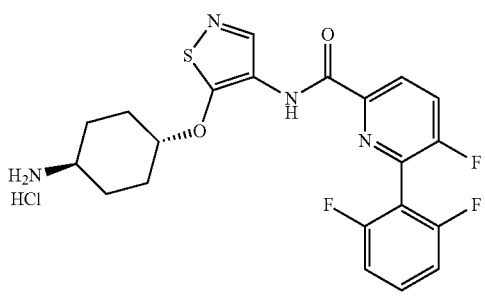

Following the procedure described in Example 1, and substituting Compound B1 in Step (1) with tert-butyl((1r,4r)-4-hydroxycyclohexyl)carbamate (B10), the title compound 10 was obtained.

Example 11

Synthesis of N-(5-((3-aminocyclohexyl)oxy)isothiazol-4-yl)-6-(2,6-difluorophenyl)-5-fluoropicolinamide hydrochloride (11)

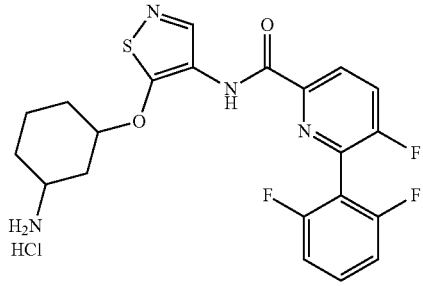

Following the procedure described in Example 1, and substituting Compound 1E in Step (1) with tert-butyl(3-hydroxycyclohexyl)carbamate (B11), the title compound 11 was obtained.

Example 12

Synthesis of N-(5-(3-aminopropoxy)isothiazol-4-yl)-6-(2,6-difluorophenyl)-5-fluoropicolinamide hydrochloride (12)

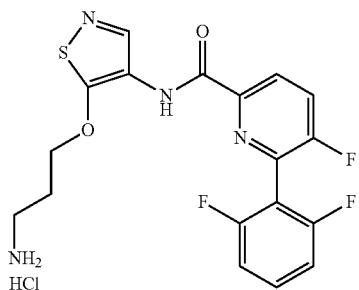

Following the procedure described in Example 1, and substituting Compound B1 in Step (1) with tert-butyl(3-hydroxypropyl)carbamate (B12), the title compound 12 was obtained.

Example 13

Synthesis of 6-(2,6-difluorophenyl)-5-fluoro-N-(5-(3-(methylamino)propoxy)isothiazol-4-yl)picolinamide hydrochloride (13)

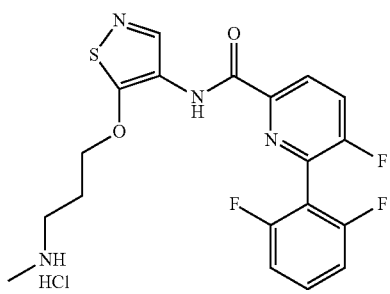

Following the procedure described in Example 1, and substituting Compound B1 in Step (1) with 3-(methylamino)propan-1-ol (B13), the title compound 13 was obtained.

Example 14

Synthesis of 6-(2,6-difluorophenyl)-N-(5-(3-(dimethylamino)propoxy)isothiazol-4-yl)-5-fluoropicolinamide hydrochloride (14)

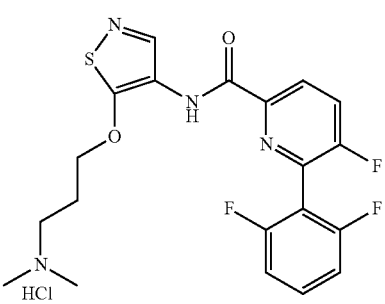

Following the procedure described in Example 1, and substituting Compound B1 in Step (1) with 3-(dimethylamino)propan-1-ol (B14), the title compound 14 was obtained.

Example 15

Synthesis of N-(5-(4-aminobutoxy)isothiazol-4-yl)-6-(2,6-difluorophenyl)-5-fluoropicolinamide hydrochloride (15)

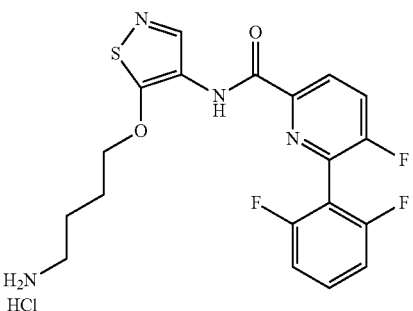

Following the procedure described in Example 1, and substituting Compound B1 in Step (1) with tert-butyl(4-hydroxybutyl)carbamate (B15), the title compound 15 was obtained.

Example 16

Synthesis of 6-(2,6-difluorophenyl)-5-fluoro-N-(5-(4-(methylamino)butoxy)isothiazol-4-yl)picolinamide hydrochloride (16)

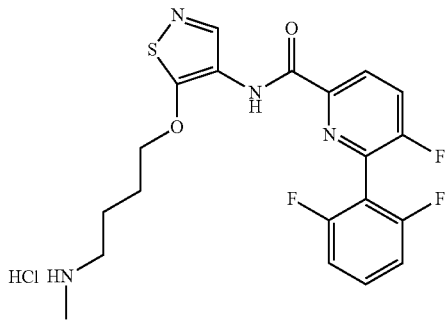

16

Following the procedure described in Example 1, and substituting Compound B1 in Step (1) with tert-butyl(4-hydroxybutyl)(methyl)carbamate (B16), the title compound 16 was obtained.

Example 17

Synthesis of 6-(2,6-difluorophenyl)-5-fluoro-N-(5-(3-hydroxypropoxy)isothiazol-4-yl)picolinamide (17)

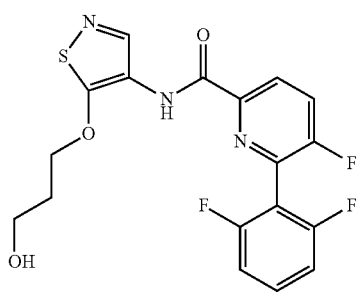

17

Following the procedure described in Example 1, and substituting Compound B1 in Step (1) with propane-1,3-diol (B17), the title compound 17 was obtained.

Example 18

Synthesis of 6-(2,6-difluorophenyl)-5-fluoro-N-(5-(3-hydroxybutoxy)isothiazol-4-yl)picolinamide (18)

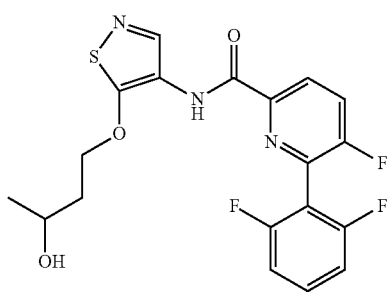

18

Following the procedure described in Example 1, and substituting Compound B1 in Step (1) with butane-1,3-diol (B18), the title compound 18 was obtained.

Example 19

Synthesis of 6-(2,6-difluorophenyl)-5-fluoro-N-(5-(4-hydroxybutoxy)isothiazol-4-yl)picolinamide (19)

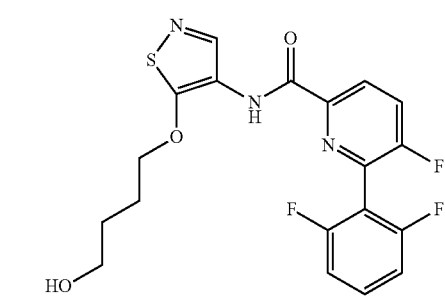

19

Following the procedure described in Example 1, and substituting Compound B1 in Step (1) with butane-1,4-diol (B4), the title compound 19 was obtained.

Example 20

Synthesis of 6-(2,6-difluorophenyl)-5-fluoro-N-(5-((4-hydroxy-4-methylpentyl)oxy)isothiazol-4-yl)picolinamide (20)

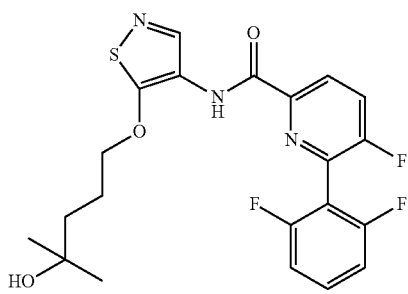

20

Following the procedure described in Example 1, and substituting Compound B1 in Step (1) with 4-methylpentane-1,4-diol (20), the title compound 20 was obtained.

Example 21

Synthesis of 6-(2,6-difluorophenyl)-N-(5-(3,4-dihydroxybutoxy)isothiazol-4-yl)-5-fluoropicolinamide (21)

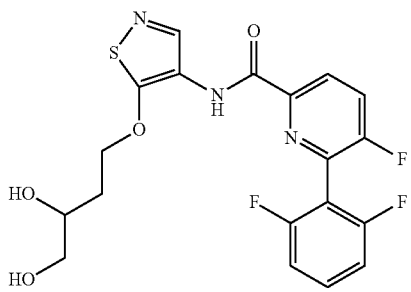

(1) Synthesis of 6-(2,6-difluorophenyl)-N-(5-(2-(2,2-dimethyl-1,3-dioxolan-4-yl)ethoxy)isothiazol-4-yl)-5-fluoropicolinamide (Protect F21)

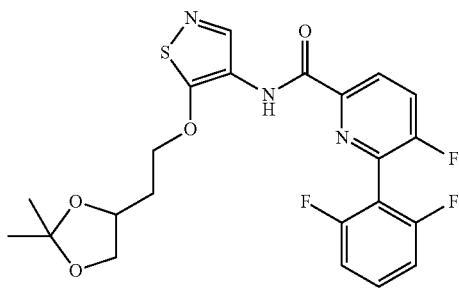

Protected F21

Following the procedure described in Example 1, Step (1) and (2), and substituting Compound B1 in Step (1) with 2-(2,2-dimethyl-1,3-dioxolan-4-yl)ethanol (B21), compound Protected F21 was obtained.

(2) Synthesis of 6-(2,6-difluorophenyl)-N-(5-(3,4-dihydroxybutoxy)isothiazol-4-yl)-5-fluoropicolinamide (21)

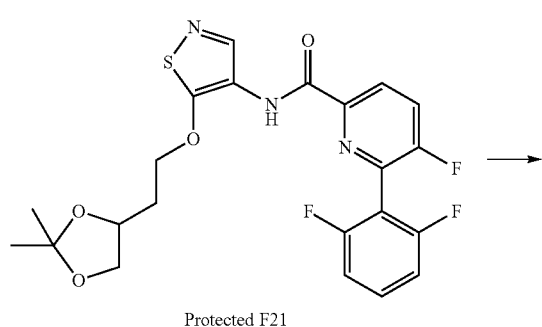

Protected F21

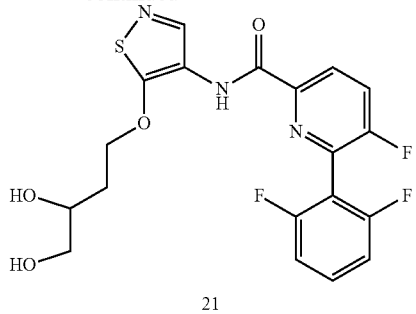

21

At room temperature (25° C.), Protected F21 (20 mg, 0.042 mmol) in methanol (2 mL) was added concentrated HCl (0.5 mL) and the solution was stirred for 4 hours. 10% Na$_2$CO$_3$ solution was added to neutralize the solution to pH=7, the water (20 mL) was added and a precipitate was formed. An off white solid product title compound 21 (14 mg, 0.032 mmol) was obtained after filtration and air drying at 25° C.

Example 22

Synthesis of 6-(2,6-difluorophenyl)-5-fluoro-N-(5-((tetrahydro-2H-pyran-4-yl)methoxy)isothiazol-4-yl)picolinamide (22)

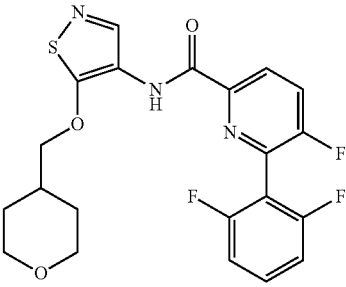

Following the procedure described in Example 1, and substituting Compound B1 in Step (1) with (tetrahydro-2H-pyran-4-yl)methanol (B22), the title compound 22 was obtained.

Example 23

Synthesis of 3-amino-6-(2,6-difluorophenyl)-5-fluoro-N-(5-(piperidin-4-ylmethoxy)isothiazol-4-yl)picolinamide hydrochloride (23)

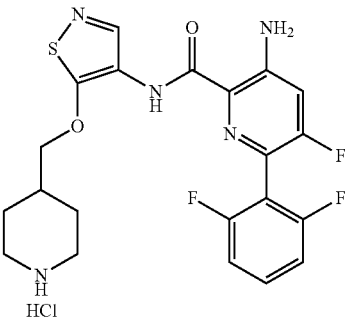

Following the procedure described in Example 1, and substituting Compound E1 in Step (3) with 3-amino-6-(2,6-difluorophenyl)-5-fluoropicolinic acid (E2), the title compound 23 was obtained.

Example 24

Synthesis of 3-amino-6-(2,6-difluorophenyl)-5-fluoro-N-(5-(pyrrolidin-3-yloxy)isothiazol-4-yl)picolinamide hydrochloride (24)

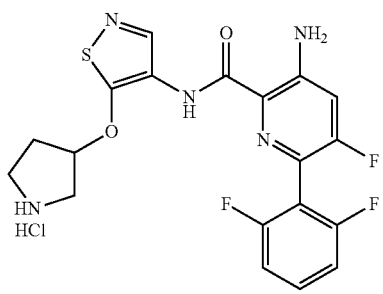

24

Following the procedure described in Example 23, and substituting Compound B1 in Step (1) with B4, the title compound 24 was obtained.

Example 25

Synthesis of 3-amino-6-(2,6-difluorophenyl)-5-fluoro-N-(5-(piperidin-4-yloxy)isothiazol-4-yl)picolinamide hydrochloride (25)

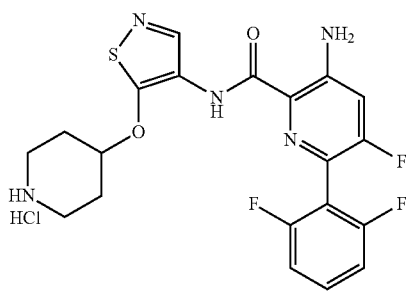

25

Following the procedure described in Example 23, and substituting Compound B1 in Step (1) with B3, the title compound 25 was obtained.

Example 26

Synthesis of 3-amino-N-(5-(azepan-4-yloxy)isothiazol-4-yl)-6-(2,6-difluorophenyl)-5-fluoropicolinamide hydrochloride (26)

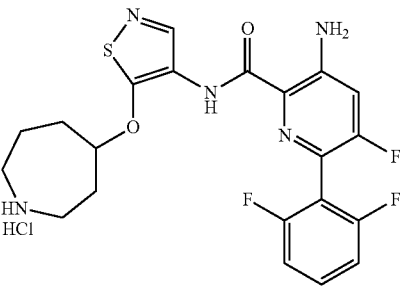

26

Following the procedure described in Example 23, and substituting Compound B1 in Step (1) with B6, the title compound 26 was obtained.

Example 27

Synthesis of 3-amino-N-(5-(((1r,4r)-4-aminocyclohexyl)oxy)isothiazol-4-yl)-6-(2,6-difluorophenyl)-5-fluoropicolinamide hydrochloride (27)

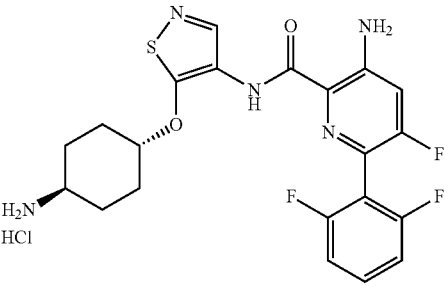

27

Following the procedure described in Example 23, and substituting Compound B1 in Step (1) with B10, the title compound 27 was obtained.

Example 28

Synthesis of 3-amino-6-(2,6-difluorophenyl)-5-fluoro-N-(5-(pyrrolidin-3-ylmethoxy)isothiazol-4-yl)picolinamide hydrochloride (28)

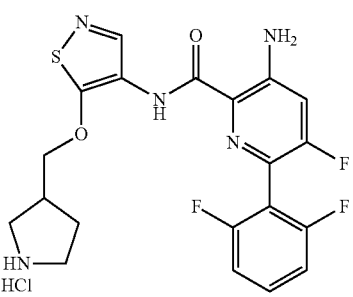

28

Following the procedure described in Example 23, and substituting Compound B1 in Step (1) with B8, the title compound 28 was obtained.

Example 29

Synthesis of N-(5-((1-amino-3-chloropropan-2-yl)oxy)isothiazol-4-yl)-6-(2,6-difluorophenyl)-5-fluoropicolinamide hydrochloride (29)

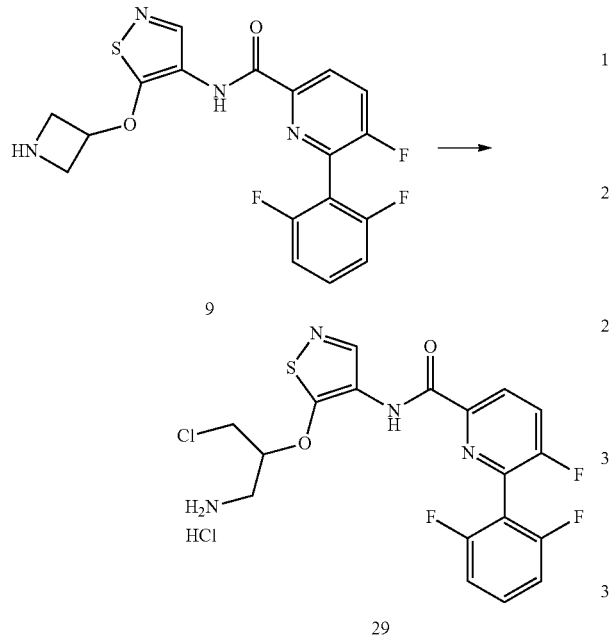

To a solution of 4M HCl in methanol (1 mL) at room temperature was added compound 9 (20 mg, 0.049 mmol). The solution was stirred for 4 hours. The solvent was then removed and the residue was washed with ether and then dried under vacuo to get an off white solid product 29 (20 mg, 0.045 mmol)

Example 30

Synthesis of N-(5-(3-amino-2-(chloromethyl)propoxy)isothiazol-4-yl)-6-(2,6-difluorophenyl)-5-fluoropicolinamide hydrochloride (30)

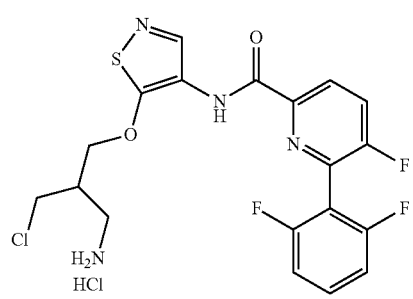

Following the procedure described in Example 29, and substituting Compound 9 with 2, the title compound 30 was obtained.

Example 31

Synthesis of 3-amino-N-(5-(azetidin-3-yloxy)isothiazol-4-yl)-6-(2,6-difluorophenyl)-5-fluoropicolinamide hydrochloride (31)

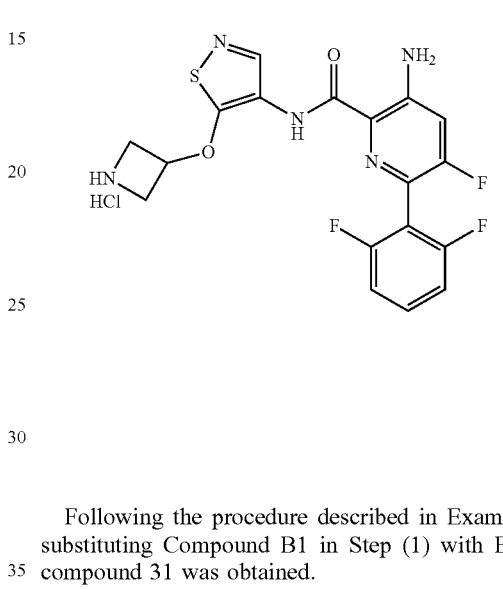

Following the procedure described in Example 23, and substituting Compound B1 in Step (1) with B9, the title compound 31 was obtained.

Example 32

Synthesis of 3-amino-N-(5-(azetidin-3-ylmethoxy)isothiazol-4-yl)-6-(2,6-difluorophenyl)-5-fluoropicolinamide hydrochloride (32)

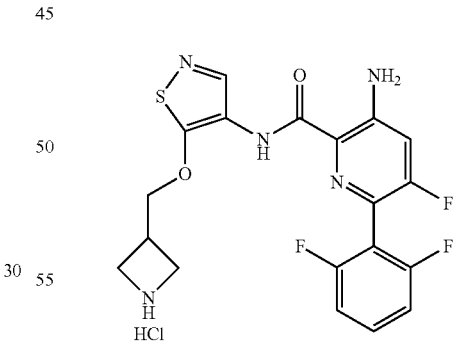

Following the procedure described in Example 23, and substituting Compound B1 in Step (1) with B2, the title compound 32 was obtained.

Example 33

Synthesis of 3-amino-N-(5-((1-amino-3-chloropropan-2-yl)oxy)isothiazol-4-yl)-6-(2,6-difluorophenyl)-5-fluoropicolinamide hydrochloride (33)

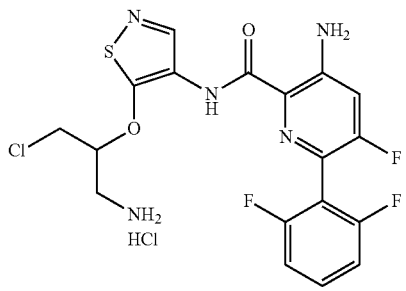

33

Following the procedure described in Example 29, and substituting Compound 9 with 31, the title compound 33 was obtained.

Example 34

Synthesis of 3-amino-N-(5-(3-amino-2-(chloromethyl)propoxy)isothiazol-4-yl)-6-(2,6-difluorophenyl)-5-fluoropicolinamide hydrochloride (34)

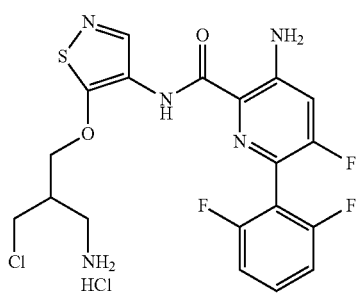

34

Following the procedure described in Example 29, and substituting Compound 9 with 32, the title compound 34 was obtained.

Example 35

Synthesis of 3-amino-6-(2,6-difluorophenyl)-5-fluoro-N-(5-(piperidin-3-ylmethoxy)isothiazol-4-yl)picolinamide hydrochloride (35)

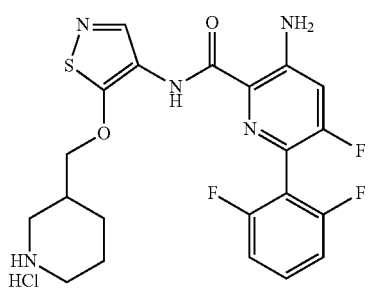

35

Following the procedure described in Example 23, and substituting Compound B1 in Step (1) with B7, the title compound 35 was obtained.

Example 36

Synthesis of 3-amino-N-(5-(4-aminobutoxy)isothiazol-4-yl)-6-(2,6-difluorophenyl)-5-fluoropicolinamide hydrochloride (36)

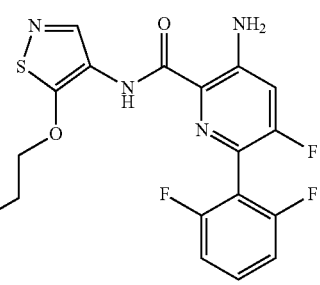

36

Following the procedure described in Example 23, and substituting Compound B1 in Step (1) with B15, the title compound 36 was obtained.

Example 37

Synthesis of 3-amino-N-(5-((3-aminocyclohexyl)oxy)isothiazol-4-yl)-6-(2,6-difluorophenyl)-5-fluoropicolinamide hydrochloride (37)

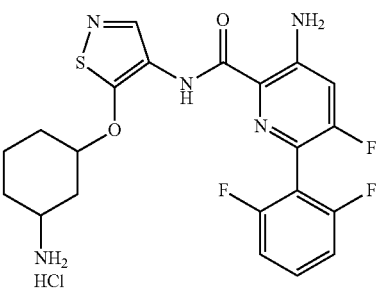

37

Following the procedure described in Example 23, and substituting Compound B1 in Step (1) with B11, the title compound 37 was obtained.

Example 38

Synthesis of 3-amino-5-fluoro-6-phenyl-N-(5-(pyrrolidin-3-yloxy)isothiazol-4-yl)picolinamide hydrochloride (38)

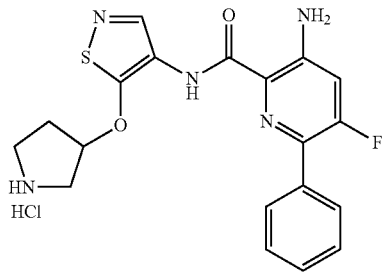

38

Following the procedure described in Example 1, substituting Compound B1 in Step (1) with tert-butyl 3-hydroxypyrrolidine-1-carboxylate (B4), and substituting Compound E1 in Step (2) with 3-amino-5-fluoro-6-phenylpicolinic acid (E3), the title compound 38 was obtained.

Example 39

Synthesis of 3-fluoro-N-(5-(piperidin-4-yloxy)isothiazol-4-yl)-[2,4'-bipyridine]-6-carboxamide hydrochloride (39)

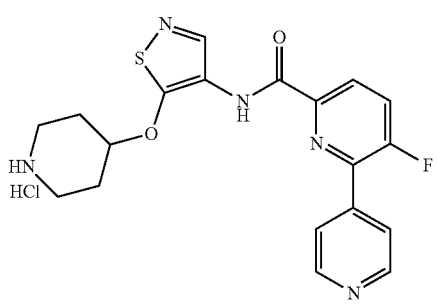

39

Following the procedure described in Example 1, substituting Compound B1 in Step (1) with tert-butyl 4-hydroxypiperidine-1-carboxylate (B3), and substituting Compound E1 in Step (2) with 3-fluoro-[2,4'-bipyridine]-6-carboxylic acid (E4), the title compound 39 was obtained.

Example 40

Synthesis of N-(5-(azepan-4-yloxy)isothiazol-4-yl)-6-(2,6-difluorophenyl)-3-fluoropicolinamide hydrochloride (40)

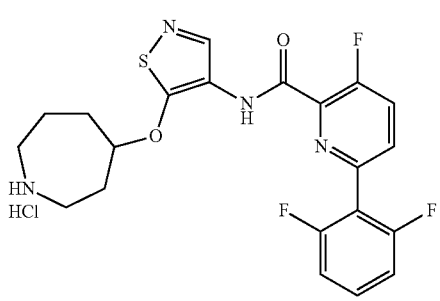

40

Following the procedure described in Example 1, substituting Compound B1 in Step (1) with tert-butyl 4-hydroxyazepane-1-carboxylate (B6), and substituting Compound E1 in Step (2) with 6-(2,6-difluorophenyl)-3-fluoropicolinic acid (E5), the title compound 39 was obtained.

Example 41

Synthesis of N-(5-(azepan-4-yloxy)isothiazol-4-yl)-5-fluoro-6-(2-fluoro-6-methoxyphenyl)picolinamide hydrochloride (41)

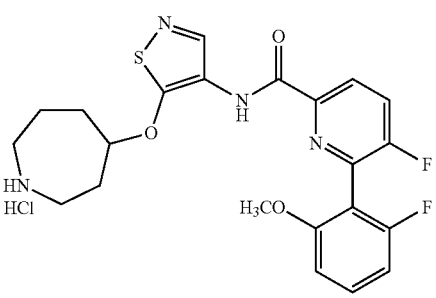

41

Compound 6 (10 mg, 0.023 mmol) was dissolved in NaOH solution in methanol (0.1M, 1 ml). The solution was stirred at 50° C. for 2 hours. Solvent was then removed. The residue was washed with water and dried under vacuum to get the title compound 41 (8 mg, 0.018 mmol)

Example 42

Synthesis of N-(5-(azepan-4-yloxy)isothiazol-4-yl)-6-(2,6-difluorophenyl)-5-(trifluoromethyl)picolinamide hydrochloride (42)

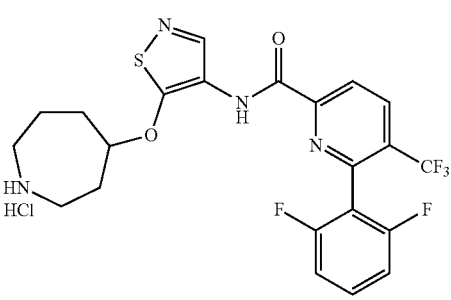

42

Following the procedure described in Example 1, substituting Compound B1 in Step (1) with tert-butyl 4-hydroxyazepane-1-carboxylate (B6), and substituting Compound E1 in Step (2) with 6-(2,6-difluorophenyl)-5-(trifluoromethyl)picolinic acid (E6), the title compound 42 was obtained.

Example 43

Synthesis of 6-(2,6-difluorophenyl)-N-(5-(piperidin-4-ylmethoxy)isothiazol-4-yl)-5-(trifluoromethyl)picolinamide hydrochloride (43)

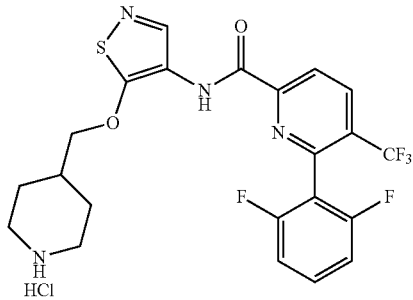

Following the procedure described in Example 1, substituting Compound E1 in Step (2) with 6-(2,6-difluorophenyl)-5-(trifluoromethyl)picolinic acid (E6), the title compound 43 was obtained.

Example 44

Synthesis of N-(5-(azetidin-3-ylmethoxy)isothiazol-4-yl)-6-(2,6-difluorophenyl)-5-(trifluoromethyl)picolinamide hydrochloride (44)

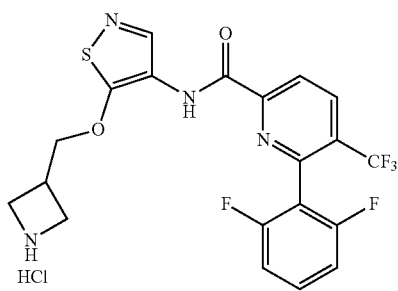

Following the procedure described in Example 1, substituting Compound B1 in Step (1) with tert-butyl 3-(hydroxymethyl)azetidine-1-carboxylate (B2), and substituting Compound E1 in Step (2) with 6-(2,6-difluorophenyl)-5-(trifluoromethyl)picolinic acid (E6), the title compound 44 was obtained.

Example 45

Synthesis of 6-(2,6-difluorophenyl)-N-(5-(piperidin-4-yloxy)isothiazol-4-yl)-5-(trifluoromethyl)picolinamide hydrochloride (45)

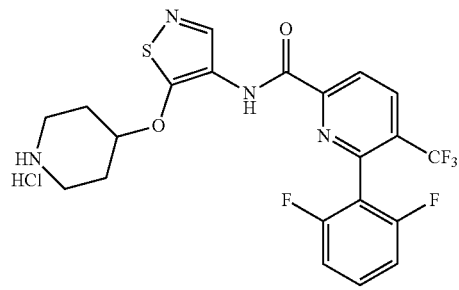

Following the procedure described in Example 1, substituting Compound B1 in Step (1) with tert-butyl 4-hydroxypiperidine-1-carboxylate (B3), and substituting Compound E1 in Step (2) with 6-(2,6-difluorophenyl)-5-(trifluoromethyl)picolinic acid (E6), the title compound 45 was obtained.

Example 46

Synthesis of N-(5-(((1r,4r)-4-aminocyclohexyl)oxy)isothiazol-4-yl)-6-(2,6-difluorophenyl)-5-(trifluoromethyl)picolinamide hydrochloride (46)

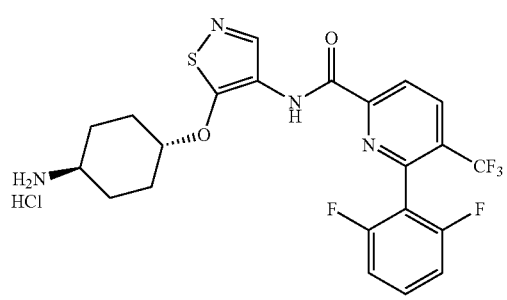

Following the procedure described in Example 1, substituting Compound B1 in Step (1) with tert-butyl((1r,4r)-4-hydroxycyclohexyl)carbamate (B10), and substituting Compound E1 in Step (2) with 6-(2,6-difluorophenyl)-5-(trifluoromethyl)picolinic acid (E6), the title compound 46 was obtained.

Example 47

Synthesis of 6-(2,6-difluorophenyl)-N-(4-((tetrahydro-2H-pyran-4-yl)methoxy)pyridin-3-yl)-5-(trifluoromethyl)picolinamide (47)

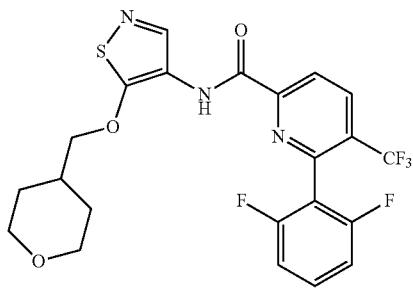

47

Following the procedure described in Example 1, substituting Compound B1 in Step (1) with (tetrahydro-2H-pyran-4-yl)methanol (B22), and substituting Compound E1 in Step (2) with 6-(2,6-difluorophenyl)-5-(trifluoromethyl)picolinic acid (E6), the title compound 47 was obtained.

Example 48

Synthesis of 3-amino-N-(5-(azepan-4-yloxy)isothiazol-4-yl)-6-(2,6-difluorophenyl)-5-(trifluoromethyl)picolinamide hydrochloride (48)

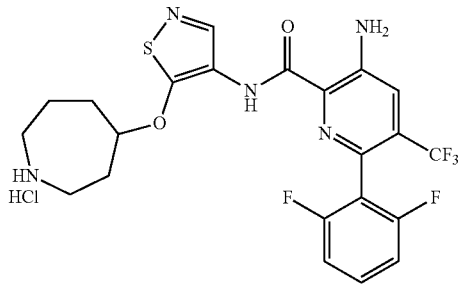

48

Following the procedure described in Example 1, substituting Compound B1 in Step (1) with tert-butyl 4-hydroxyazepane-1-carboxylate (B6), and substituting Compound E1 in Step (2) with 3-amino-6-(2,6-difluorophenyl)-5-(trifluoromethyl)picolinic acid (E7), the title compound 48 was obtained.

Example 49

Synthesis of 3-amino-6-(2,6-difluorophenyl)-N-(5-(piperidin-4-ylmethoxy)isothiazol-4-yl)-5-(trifluoromethyl)picolinamide hydrochloride (49)

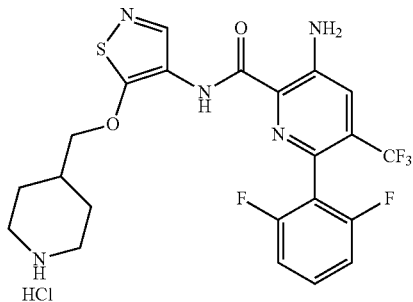

49

Following the procedure described in Example 1, substituting Compound E1 in Step (2) with 3-amino-6-(2,6-difluorophenyl)-5-(trifluoromethyl)picolinic acid (E7), the title compound 49 was obtained

Example 50

Synthesis of 3-amino-N-(5-(azetidin-3-ylmethoxy)isothiazol-4-yl)-6-(2,6-difluorophenyl)-5-(trifluoromethyl)picolinamide hydrochloride (50)

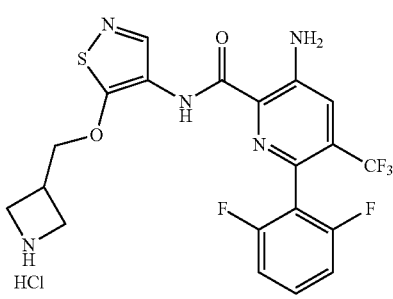

50

Following the procedure described in Example 1, substituting Compound B1 in Step (1) with tert-butyl 3-(hydroxymethyl)azetidine-1-carboxylate (B2), and substituting Compound E1 in Step (2) with 3-amino-6-(2,6-difluorophenyl)-5-(trifluoromethyl)picolinic acid (E7), the title compound 50 was obtained.

Example 51

Synthesis of 3-amino-6-(2,6-difluorophenyl)-N-(5-(piperidin-4-yloxy)isothiazol-4-yl)-5-(trifluoromethyl)picolinamide hydrochloride (51)

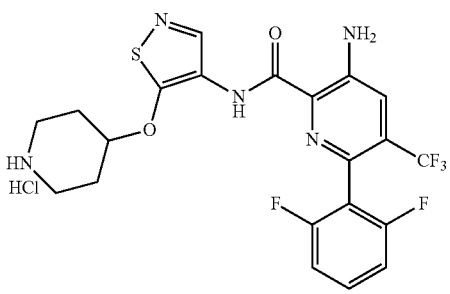

51

Following the procedure described in Example 1, substituting Compound B1 in Step (1) with tert-butyl 4-hydroxypiperidine-1-carboxylate (B3), and substituting Compound E1 in Step (2) with 3-amino-6-(2,6-difluorophenyl)-5-(trifluoromethyl)picolinic acid (E7), the title compound 51 was obtained.

Example 52

Synthesis of 3-amino-N-(5-(((1r,4r)-4-aminocyclohexyl)oxy)isothiazol-4-yl)-6-(2,6-difluorophenyl)-5-(trifluoromethyl)picolinamide hydrochloride (52)

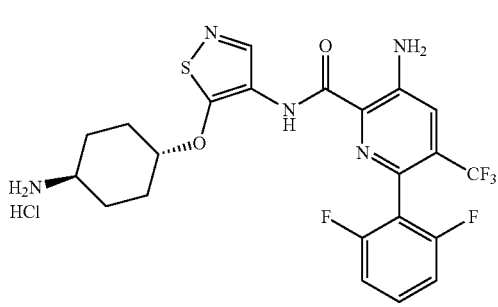

Following the procedure described in Example 1, substituting Compound B1 in Step (1) with tert-butyl((1r,4r)-4-hydroxycyclohexyl)carbamate (B10), and substituting Compound E1 in Step (2) with 3-amino-6-(2,6-difluorophenyl)-5-(trifluoromethyl)picolinic acid (E7), the title compound 52 was obtained.

Example 53

Synthesis of 3-amino-6-phenyl-N-(5-(pyrrolidin-3-yloxy)isothiazol-4-yl)-5-(trifluoromethyl)picolinamide hydrochloride (53)

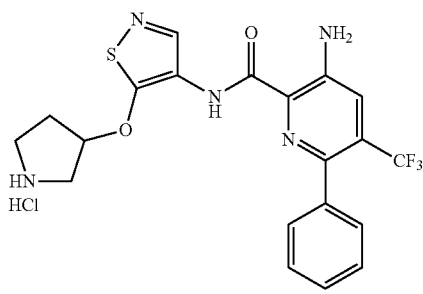

Following the procedure described in Example 1, substituting Compound B1 in Step (1) with tert-butyl 3-hydroxypyrrolidine-1-carboxylate (B4), and substituting Compound E1 in Step (2) with 3-amino-6-(2,6-difluorophenyl)-5-(trifluoromethyl)picolinic acid (E7), the title compound 53 was obtained.

Example 54

Synthesis of N-(5-(3-amino-2-(chloromethyl)propoxy)isothiazol-4-yl)-6-(2,6-difluorophenyl)-5-(trifluoromethyl)picolinamide hydrochloride (54)

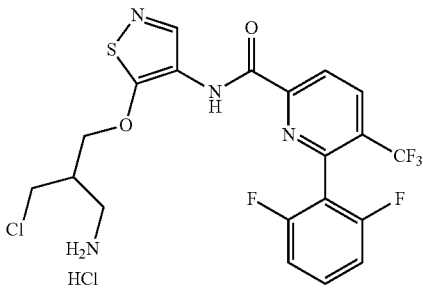

Following the procedure described in Example 29, substituting Compound 9 with Compound 44, the title compound 54 was obtained.

Example 55

Synthesis of 3-amino-N-(5-(3-amino-2-(chloromethyl)propoxy)isothiazol-4-yl)-6-(2,6-difluorophenyl)-5-(trifluoromethyl)picolinamide hydrochloride (55)

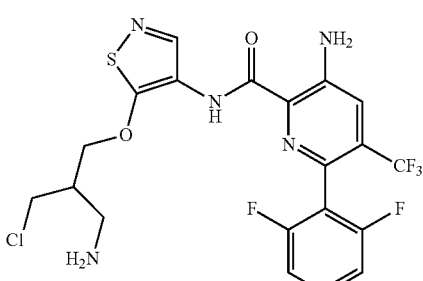

Following the procedure described in Example 29, substituting Compound 9 with Compound 50, the title compound 55 was obtained.

Example 56

Synthesis of N-(5-(3-amino-2-(hydroxymethyl)propoxy)isothiazol-4-yl)-6-(2,6-difluorophenyl)-5-fluoropicolinamide hydrochloride (56)

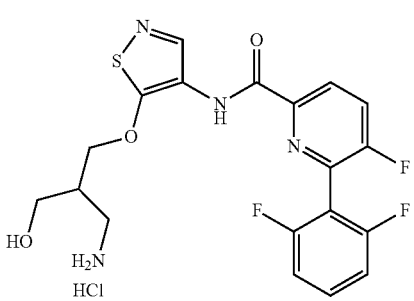

To a solution of 1:1 TFA and methanol (1 ml) was added Compound 2 (40 mg, 0.096 mmol) and stirred at room temperature for 4 hour. The solution was then neutralized with saturated Na2CO3 and the solvent was removed. The residue was purified by flash chromatography (1:1 ethyl acetate/petroleum ether) to get the Compound 56 (10 mg, 0.023 mmol).

Example 57

Synthesis of 3-amino-N-(5-(3-amino-2-(hydroxymethyl)propoxy)isothiazol-4-yl)-6-(2,6-difluorophenyl)-5-fluoropicolinamide hydrochloride (57)

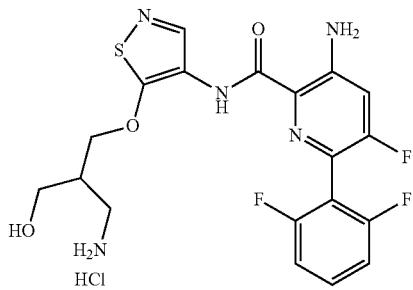

Following the procedure described in Example 56, substituting Compound 2 with Compound 32, the title compound 57 was obtained.

Example 58

Synthesis of N-(5-(3-amino-2-(hydroxymethyl)propoxy)isothiazol-4-yl)-6-(2,6-difluorophenyl)-5-(trifluoromethyl)picolinamide hydrochloride (58)

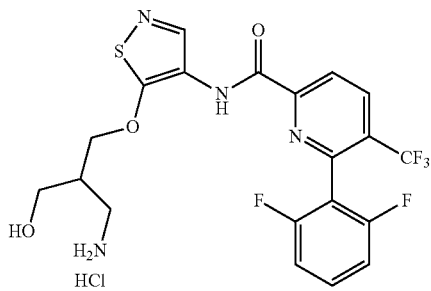

Following the procedure described in Example 56, substituting Compound 2 with Compound 44, the title compound 58 was obtained.

Example 59

Synthesis of 3-amino-N-(5-(3-amino-2-(hydroxymethyl)propoxy)isothiazol-4-yl)-6-(2,6-difluorophenyl)-5-(trifluoromethyl)picolinamide hydrochloride (59)

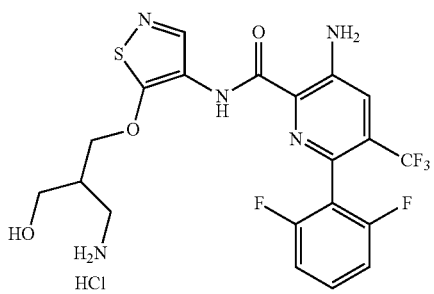

Following the procedure described in Example 56, substituting Compound 2 with Compound 50, the title compound 59 was obtained.

Example 60

Synthesis of N-(5-((3-aminocyclohexyl)oxy)isothiazol-4-yl)-6-(2,6-difluorophenyl)-5-(trifluoromethyl)picolinamide hydrochloride (60)

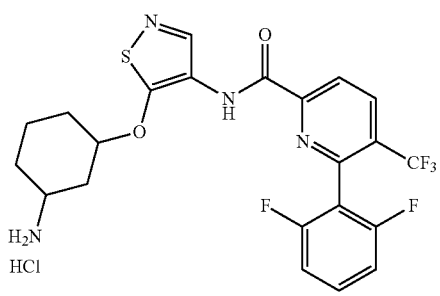

Following the procedure described in Example 1, substituting Compound B1 in Step (1) with tert-butyl(3-hydroxycyclohexyl)carbamate (B11), and substituting Compound E1 in Step (2) with 6-(2,6-difluorophenyl)-5-(trifluoromethyl)picolinic acid (E6), the title compound 47 was obtained.

Example 61

Synthesis of 3-amino-N-(5-((3-aminocyclohexyl)oxy)isothiazol-4-yl)-6-(2,6-difluorophenyl)-5-(trifluoromethyl)picolinamide hydrochloride (61)

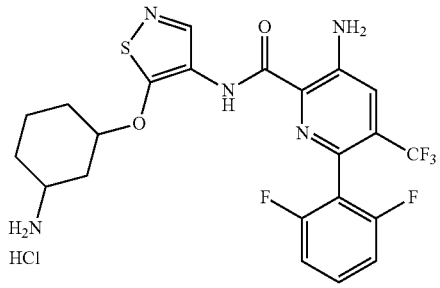

Following the procedure described in Example 1, substituting Compound B1 in Step (1) with tert-butyl(3-hydroxycyclohexyl)carbamate (B11), and substituting Compound E1 in Step (2) with 3-amino-6-(2,6-difluorophenyl)-5-(trifluoromethyl)picolinic acid (E7), the title compound 61 was obtained.

Example 62

The ΔF508 mutant CFTR activities of the CFTR modulators are detected using the Fluorescence Assay developed by Pedemonte (Pedemonte N., et al., Antihypertensive 1,4-dihydropyridines as correctors of the cystic fibrosis transmembrane conductance regulator channel gating defect caused by cystic fibrosis mutations, *Mol. Pharmacol.*, 2005, 68, 1736-1746).

Cell Culture

Fischer rat thyroid (FRT) cells, stably transfected with ΔF508 were retransfected with the YFP-H148Q/I152L fluorescent protein. The cells were plated (100,000 cells/well) on black 96-well microplates with clear plastic bottom (Corning Life Sciences, Acton, Mass.).

Fluorescence Assay

The 96-well microplates containing FRT cells expressing F508-CFTR and the halide-sensitive YFP were incubated at 27° C. for 20 to 24 h to allow rescue of the mutant protein to the plasma membrane. After incubation, cells were washed with PBS (containing 137 mM NaCl, 2.7 mM KCl, 8.1 mM Na2HPO4, 1.5 mM KH2PO4, 1 mM CaCl2, and 0.5 mM MgCl2) and stimulated for 20 min with forskolin (20 μM) and test compounds (20 μM) in a final volume of 60 Microplates were then transferred to a microplate reader for CFTR activity determination. Each assay consisted of a continuous 14-s fluorescence reading (5 points per second) with 2 s before and 12 s after injection of 165 μl of an iodide-containing solution (PBS with Cl⁻ replaced by D. Final iodide concentration in the wells was 100 mM. These data were normalized to the initial background subtracted fluorescence. To determine I⁻ influx rate, the final 11 s of the data for each well were fitted with an exponential function to extrapolate initial slope. CFTR activity was determined by measuring the rate of fluorescence quenching induced by extracellular addition of I⁻. Data are normalized to the mean activity measured in the presence of forskolin alone.

TABLE I

Analytical and CFTR activity data of the compounds described in the examples of the present invention

| Name | NMR | MS | CFTR Activity |
|---|---|---|---|
| 6-(2,6-difluorophenyl)-5-fluoro-N-(5-(piperidin-4-ylmethoxy)isothiazol-4-yl)picolinamide hydrochloride | 1H NMR (400 MHz, DMSO-d6) δ: 1.34 (bs, 2H), 1.78 (bs, 2H), 2.69 (bs, 3H), 3.12 (bs, 2H), 4.11 (bs, 2H), 7.37 (t, J = 8, 2H), 7.67-7.75 (m, 1H), 8.21 (t, J = 10, 1H), 8.35 (dd, J = 8, 4, 1H), 8.54 (s, 1H), 8.60 (bs, 1H), 8.75 (bs, 1H), 10.10 (s, 1H) | 449 (M + 1) | 0.9 |
| N-(5-(azetidin-3-ylmethoxy)isothiazol-4-yl)-6-(2,6 difluorophenyl)-5-fluoropicolinamide hydrochloride | 1H NMR (400 MHz, CDCl3) δ: 1.99 (bs, 1H), 3.60-4.40 (m, 4H), 4.45 (bs, 2H), 7.11 (t, J = 8, 2H), 7.45-7.65 (m, 1H), 7.69 (t, J = 8, 1H), 8.29 (dd, J = 8, 4, 1H), 8.86 (bs, 1H), 9.49 (bs, 1H) | 421 (M + 1) | 0.2 |
| 6-(2,6-difluorophenyl)-5-fluoro-N-(5-(piperidin-4-yloxy)isothiazol-4-yl)picolinamide hydrochloride | 1H NMR (400 MHz, DMSO-d6) δ: 1.95-2.05 (m, 2H). 2.10-2.20 (m, 2H), 3.11-3.13-(m, 2H), 3.23-3.25 (m, 2H), 4.58-4.60 (m, 1H), 7.38 (t, J = 8, 2H), 7.68-7.74 (m, 1H), 8.21 (t, J = 10, 1H), 8.33 (dd, J = 8, 4, 1H), 8.53 (s, 1H), 8.65 (bs, 2H), 10.11 (s, 1H), | 435 (M + 1) | 1.3 |
| 6-(2,6-difluorophenyl)-5-fluoro-N-(5-(pyrrolidin-3-yloxy)isothiazol-4-yl)picolinamide hydrochloride | 1H NMR (400 MHz, DMSO-d6) δ: 2.05-2.35 (m, 4H), 5.12 (bs, 1H), 5.26 (s, 1H), 7.37 (t, J = 8, 2H), 7.67-7.75 (m, 1H), 8.21 (t, J = 10, 1H), 8.35 (dd, J = 8, 4, 1H), 9.39 (bs, 1H), 9.86 (bs, 1H), 10.11 (s, 1H) | 421 (M + 1) | 0.8 |
| 6-(2,6-difluorophenyl)-5-fluoro-N-(5-(piperidin-3-yloxy)isothiazol-4-yl)picolinamide hydrochloride | 1H NMR (400 MHz, DMSO-d6) δ: 1.60-1.80 (m, 1H), 1.80-2.01 (m, 3H), 3.05 (bs, 2H), 3.57 (s, 2H), 4.67 (bs, 1H), 7.37 (t, J = 8, 2H), 7.67-7.75 (m, 1H), 8.21 (t, J = 10, 1H), 8.35 (dd, J = 8, 4, 1H), 8.67 (s, 1H), 8.80 (bs, 1H), 9.34 (bs, 1H), 10.18 (s, 1H) | 435 (M + 1) | 0.5 |
| N-(5-(azepan-4-yloxy)isothiazol-4-yl)-6-(2,6-difluorophenyl)-5-fluoropicolinamide hydrochloride | 1H NMR (400 MHz, DMSO-d6) δ: 1.70-2.40 (m, 6H), 3.00-3.30 (m, 4H), 4.59 (bs, 1H), 7.39 (t, J = 8, 2H), 7.67-7.75 (m, 1H), 8.21 (t, J = 10, 1H), 8.33 (dd, J = 8, 4, 1H), 8.57 (s, 1H), 9.09 (bs, 1H), 9.18 (bs, 1H), 10.02 (s, 1H) | 449 (M + 1) | 1.4 |
| 6-(2,6-difluorophenyl)-5-fluoro-N-(5-(piperidin-3-ylmethoxy)isothiazol-4-yl)picolinamide hydrochloride | 1H NMR (400 MHz, DMSO-d6) δ: 1.30-1.40 (m, 1H), 1.55-1.75 (m, 1H), 1.75-1.85 (m, 2H), 2.70-2.90 (m, 1H), 3.25 (d, j = 8, 2H), 4.18 (bs, 2H), 7.38 (t, J = 8, 2H), 7.67-7.75 (m, 1H), 8.20 (t, J = 10, 1H), 8.33 (dd, J = 8, 4, 1H), 8.54 (bs, 2H), 8.75 (bs, 1H), 10.05 (s, 1H) | 449 (M + 1) | 0.9 |
| 6-(2,6-difluorophenyl)-5-fluoro-N-(5-(pyrrolidin-3-ylmethoxy)isothiazol-4-yl)picolinamide hydrochloride | 1H NMR (400 MHz, CDCl3) δ: 2.00 (bs, 1H), 2.31 (bs, 12H), 2.99 (bs, 1H), 3.20-3.60 (m, 4H), 4.26 (bs, 2H), 7.17 (t, J = 8, 2H), 7.45-7.60 (m, 1H), 7.77 (t, J = 8, 1H), 8.40 (bs, 1H), 8.91 (s, 1H), 9.56 (s, 1H) | 435 (M + 1) | 0.7 |

TABLE I-continued

Analytical and CFTR activity data of the compounds described in the examples of the present invention

| Name | NMR | MS | CFTR Activity |
|---|---|---|---|
| N-(5-(azetidin-3-yloxy)isothiazol-4-yl)-6-(2,6-difluorophenyl)-5-fluoropicolinamide hydrochloride | 1H NMR (400 MHz, CDCl3) δ: 3.10-3.60 (m, 3H), 3.95-4.40 (m, 1H), 4.80-5.20 (m, 1H), 7.11 (t, J = 8, 2H), 7.45-7.65 (m, 1H), 7.76 (t, J = 8, 1H), 8.40 (dd, J = 8, 4, 1H), 9.03 (s, 0.7H), 9.08 (s, 0.3H), 9.53 (bs, 1H) | 407 (M + 1) | 0.1 |
| N-(5-(((1r,4r)-4-aminocyclohexyl)oxy)isothiazol-4-yl)-6-(2,6-difluorophenyl)-5-fluoropicolinamide hydrochloride | 1H NMR (400 MHz, DMSO) δ: 1.10-1.51 (m, 2H), 1.64-1.69 (m, 2H), 1.98-2.02 (m, 2H), 2.20-2.23 (m, 2H), 2.84-2.90 (m, 1H), 4.35-4.41 (m, 1H), 7.38 (t, J = 8, 2H), 7.67-7.75 (m, 1H), 8.20 (t, J = 10, 1H), 8.33 (dd, J = 8, 4, 1H), 8.55 (s, 1H), 8.95 (bs, 1H), 9.10 (bs, 1H), 10.13 (s, 1H) | 449 (M + 1) | 1 |
| N-(5-((3-aminocyclohexyl)oxy)isothiazol-4-yl)-6-(2,6-difluorophenyl)-5-fluoropicolinamide hydrochloride | 1H NMR (400 MHz, CDCl3) δ: 1.05-2.00 (m, 5H), 2.60-2.80 (m, 3H), 3.05-3.50 (m, 1H), 3.95-4.05 (m, 0.7H), 4.48 (bs, 0.3H), 7.01 (t, J = 8, 2H), 7.60-7.70 (m, 1H), 8.29 (dd, J = 8, 4, 1H), 8.97 (s, 0.7H), 9.03 (s, 0.3H), 9.52 (bs, 1H) | 449 (M + 1) | 1.1 |
| N-(5-(3-aminopropoxy)isothiazol-4-yl)-6-(2,6-difluorophenyl)-5-fluoropicolinamide hydrochloride | 1H NMR (400 MHz, CD3OD) δ: 1.86 (bs, 2H), 2.81 (bs, 2H), 4.21 (bs, 2H), 7.30 (t, J = 8, 2H), 7.57-7.77 (m, 1H), 8.05 (t, J = 8, 1H), 8.40 (dd, J = 8, 4, 1H), 9.10 (s, 1H) | 409 (M + 1) | 0.7 |
| 6-(2,6-difluorophenyl)-5-fluoro-(N-(5-(3-(methylamino)propoxy)isothiazol-4-yl)picolinamide hydrochloride | 1H NMR (400 MHz, CD3OD) δ: 1.91 (bs, 2H), 2.81 (bs, 2H), 2.85 (s, 3H), 4.22 (bs, 2H), 7.29 (t, J = 8, 2H), 7.56-7.75 (m, 1H), 8.15 (t, J = 8, 1H), 8.41 (dd, J = 8, 4, 1H), 9.08 (s, 1H) | 423 (M + 1) | 0.5 |
| 6-(2,6-difluorophenyl)-N-(5-(3-(dimethylamino)propoxy)isothiazol-4-yl)-5-fluoropicolinamide hydrochloride | 1H NMR (400 MHz, CD3OD) δ: 1.90 (bs, 2H), 2.80 (bs, 2H), 2.90 (s, 6H), 4.20 (bs, 2H), 7.31 (t, J = 8, 2H), 7.55-7.75 (m, 1H), 8.21 (t, J = 8, 1H), 8.40 (dd, J = 8, 4, 1H), 9.11 (s, 1H) | 437 (M + 1) | 0.3 |
| N-(5-(4-aminobutoxy)isothiazol-4-yl)-6-(2,6-difluorophenyl)-5-fluoropicolinamide hydrochloride | 1H NMR (400 MHz, CD3OD) δ: 1.51-1.60 (m, 2H), 1.75-1.79 (m, 2H), 2.81-2.83 (m, 2H), 4.21 (t, J = 8 Hz, 2H), 7.32 (t, J = 8, 2H), 7.55-7.75 (m, 1H), 8.20 (t, J = 8, 1H), 8.39 (dd, J = 8, 4, 1H), 9.12 (s, 1H) | 443 (M + 1) | 0.7 |
| 6-(2,6-difluorophenyl)-5-fluoro-N-(5-(4-(methylamino)butoxy)isothiazol-4-yl)picolinamide hydrochloride | 1H NMR (400 MHz, CD3OD) δ: 1.50-1.61 (m, 2H), 1.75-1.80 (m, 2H), 2.81-2.83 (m, 2H), 2.92 (s, 3H), 4.21 (t, J = 8 Hz, 2H), 7.30 (t, J = 8, 2H), 7.55-7.75 (m, 1H), 8.21 (t, J = 8, 1H) 8.40 (dd, J = 8, 4, 1H), 9.09 (s, 1H) | 437 (M + 1) | 0.5 |
| 6-(2,6-difluorophenyl)-5-fluoro-N-(5-(3-hydroxypropoxy)isothiazol-4-yl)picolinamide | 1H NMR (400 MHz, DMSO-d6) δ: 1.90 (bs, 2H), 3.66 (bs, 2H), 4.27 (bs, 2H), 4.63 (s, 1H), 7.38 (t, J = 8, 2H), 7.65-7.75 (m, 1H), 8.20 (t, J = 8, 1H), 8.32 (dd, J = 8, 4, 1H), 8.56 (s, H), 10.10 (s, 1H) | 410 (M + 1) | 0.1 |
| 6-(2,6-difluorophenyl)-5-fluoro-N-(5-(3-hydroxybutoxy)isothiazol-4-yl)picolinamide | 1H NMR (400 MHz, CD3OD) δ: 1.02 (s, 3H), 1.60-1.78 (m, 2H), 3.40-3.55 (m, 1H), 4.10-4.25 (m, 2H), 7.30 (t, J = 8, 2H), 7.55-7.75 (m, 1H), 8.21 (t, J = 8, 1H), 8.39 (dd, J = 8, 4, 1H), 9.10 (s, 1H) | 424 (M + 1) | 0.12 |
| 6-(2,6-difluorophenyl)-5-fluoro-N-(5-(4-hydroxybutoxy)isothiazol-4-yl)picolinamide | 1H NMR (400 MHz, CD3OD) δ: 1.45-1.52 (m, 2H), 1.74-1.78 (m, 2H), 3.36-3.45 (m, 2H), 4.21 (t, J = 8, 2H), 7.30 (t, J = 8, 2H), 7.55-7.75 (m, 1H), 8.21 (t, J = 8, 1H), 8.40 (dd, J = 8, 4, 1H), 9.09 (s, 1H) | 424 (M + 1) | 0.1 |
| 6-(2,6-difluorophenyl)-5-fluoro-N-(5-((4-hydroxy-4-methylpentyl)oxy)isothiazol-4-yl)picolinamide | 1H NMR (400 MHz, CD3OD) δ: 1.00 (s, 6H), 1.45-1.52 (t, J = 8, 2H), 1.75-1.78 (m, 2H), 4.21 (t, J = 8, 2H), 7.30 (t, J = 8, 2H), 7.55-7.75 (m, 1H), 8.20 (t, J = 8, 1H), 8.41 (dd, J = 8, 4, 1H), 9.10 (s, 1H) | 452 (M + 1) | 0.1 |
| 6-(2,6-difluorophenyl)-N-(5-(3,4-dihydroxybutoxy)isothiazol-4-yl) 5-fluoropicolinamide | 1H NMR (400 MHz, CD3OD) δ: 1.88-2.05 (m, 2H), 3.28 (bs, 2H), 3.70 (bs, 1H), 4.15-4.35 (m, 2H), 7.31 (t, J = 8, 2H), 7.56-7.75 (m, 1H), 8.20 (t, J = 8, 1H), 8.39 (dd, J = 8, 4, 1H), 9.11 (s, 1H) | 440 (M + 1) | 0.5 |
| 6-(2,6-difluorophenyl)-5-fluoro-N-(5-((tetrahydro-2H-pyran-4-yl)methoxy)isothiazol-4-yl)picolinamide | 1H NMR (400 MHz, DMSO-d6) δ: 1.68-1.85 (m, 1H), 2.23-2.38 (m, 2H), 2.60-2.70 (m, 2H), 3.75-3.85 (m, 2H), 3.97-4.05 (m, 4H), 7.38 (t, J = 8, 2H), 7.67-7.75 (m, 1H), .20 (t, J = 10, 1H), 8.32 (dd, J = 8, 4, 1H), 8.56 (s, 1H), 10.10 (s, 1H) | 450 (M + 1) | 0.3 |
| 3-amino-6-(2,6-difluorophenyl)-5-fluoro-N-(5-(piperidin-4-ylmethoxy)isothiazol-4-yl)picolinamide hydrochloride | 1H NMR (400 MHz, DMSO-d6) δ: 1.34 (bs, 2H), 1.78 (bs, 2H), 2.69 (bs, 3H), 3.12 (bs, 2H), 4.11 (bs, 2H), 7.22 (bs, 2H), 7.37 (t, J = 8, 2H), 7.52-7.62 (m, 1H), 8.40 (d, J = 10, 1H), 8.80 (s, 1H), 9.36 (bs, 1H), 9.66 (bs, 1H), 10.12 (s, 1H) | 464 (M + 1) | 2.2 |
| 3-amino-6-(2,6-difluorophenyl)-5-fluoro-N-(5-(pyrrolidin-3-yloxy)isothiazol-4-yl)picolinamide hydrochloride | 1H NMR (400 MHz, DMSO-d6) δ: 2.05-2.35 (m, 4H), 5.12 (bs, 1H), 5.26 (s, 1H), 7.23 (bs, 2H), 7.36 (t, J = 8, 2H), 7.50-7.60 (m, 1H), 8.41 (d, J = 10, 1H), 8.80 (s, 1H), 9.06 (bs, 1H), 9.32 (bs, 1H), 10.11 (s, 1H) | 436 (M + 1) | 1.9 |
| 3-amino-6-(2,6-difluorophenyl)-5-fluoro-N-(5-(piperidin-4-yloxy)isothiazol-4-yl)picolinamide hydrochloride | 1H NMR (400 MHz, DMSO-d6) δ: 1.95-2.05 (m, 2H). 2.10-2.20 (m, 2H), 3.11-3.13-(m, 2H), 3.23-3.25 (m, 2H), 4.58-4.60 (m, 1H), 7.20 (bs, 2H), 7.36 (t, J = 8, 2H), 7.51-7.62 (m, 1H), 8.41 (d, J = 10, 1H), 8.81 (s, 1H), 9.16 (bs, 1H), 9.30 (bs, 1H), 10.10 (s, 1H) | 450 (M + 1) | 2.5 |
| 3-amino-N-(5-(azepan-4-yloxy)isothiazol-4-yl)-6-(2,6-difluorophenyl)-5-fluoropicolinamide hydrochloride | 1H NMR (400 MHz, DMSO-d6) δ: 1.70-2.40 (m, 6H), 3.00-3.30 (m, 4H), 4.59 (bs, 1H), 7.22 (bs, 2H), 7.36 (t, J = 8, 2H), 7.55-7.65 (m, 1H), 8.41 (d, J = 10, 1H), 8.80 (s, 1H), 9.18 (bs, 1H), 9.30 (bs, 1H), 10.10 (s, 1H) | 464 (M + 1) | 3.1 |
| 3-amino-N-(5-(((1r,4r)-4-aminocyclohexyl)oxy)isothiazol-4-yl)-6-(2,6-difluorophenyl)-5-fluoropicolinamide hydrochloride | 1H NMR (400 MHz, DMSO) δ: 1.10-1.51 (m, 2H), 1.64-1.69 (m, 2H), 1.98-2.02 (m, 2H), 2.20-2.23 (m, 2H), 2.84-2.90 (m, 1H), 4.35-4.41 (m, 1H), 7.22 (bs, 2H), 7.36 (t, J = 8, 2H), 7.54-7.65 (m, 1H), 8.05 (bs, 3H), 8.41 (d, J = 10, 1H), 8.81 (s, 1H), 10.09 (s, 1H) | 464 (M + 1) | 2.8 |

TABLE I-continued

Analytical and CFTR activity data of the compounds described in the examples of the present invention

| Name | NMR | MS | CFTR Activity |
|---|---|---|---|
| 3-amino-6-(2,6-difluorophenyl)-5-fluoro-N-(5-(pyrrolidin-3-ylmethoxy)isothiazol-4-yl)picolinamide hydrochloride | 1H NMR (400 MHz, DMSO-d6) δ: 1.65-1.74 (m, 1H), 2.10-2.17 (m, 1H), 2.70-2.78 (m, 1H), 2.83-2.97 (m, 2H), 3.02-3.08 (m, 1H), 3.16-3.21 (m, 1H), 4.43-4.45 (m, 2H), .20-7.31 (m, 3H), 7.35 (d, 1H), 7.36 (bs, 2H), 7.50-7.62 (m, 1H), 8.43 (dd, J = 8, 4,1H), 8.81 (s, 1H), 9.04 (bs, 2H), 10.18 (s, 1H) | 450 (M + 1) | 1.7 |
| N-(5-((1-amino-3-chloropropan-2-yl)oxy)isothiazol-4-yl)-6-(2,6-difluorophenyl)-5-fluoropicolinamide hydrochloride | 1H NMR (400 MHz, CDCl3) δ: 2.23 (bs, 3H), 3.14 (dd, J = 12, 8, 1H), 3.23 (dd, J = 10, 4, 1H), 3.51 (s, 1H), 3.78 (d, J = 8, 2H), 4.15-4.31 (m, 1H), 7.10 (t, J = 8, 2H), 7.46-7.53 (m, 1H), 7.74 (t, J = 10, 1H), 8.40 (dd, J = 8, 4, 1H), 9.08 (s, 1H), 10.05 (bs, 1H) | 443 (M + 1) | 1.4 |
| N-(5-(3-amino-2-(chloromethyl)propoxy)isothiazol-4-yl)-6-(2,6-difluorophenyl)-5-fluoropicolinamide hydrochloride | 1H NMR (400 MHz, CDCl3) δ: 2.30-2.70 (m, 4H), 2.90-3.05 (m, 1H), 3.65 (s, 1H), 3.79 (d, J = 8, 2H), 4.20-4.40 (m, 2H), 7.12 (t, J = 8, 2H), 7.46-7.53 (m, 1H), 7.74 (t, J = 10, 1H), 8.39 (dd, J = 8, 4, 1H), 9.65 (bs, 1H) | 457 (M + 1) | 1.4 |
| 3-amino-N-(5-(azetidin-3-yloxy)isothiazol-4-yl)-6-(2,6-difluorophenyl)-5-fluoropicolinamide hydrochloride | 1H NMR (400 MHz, DMSO-d6) δ: 3.97-4.00 (m, 2H), 4.49-4.52 (m, 2H), 5.40-5.41 (m, 1H), 7.20-7.30 (m, 2H), 7.30 (d, 1H), 7.36 (bs, 2H), 7.50-7.60 (m, 1H), 8.40 (dd, J = 8, 4, 1H), 8.75 (s, 1H), 9.45 (bs, 2H), 10.45 (s, 1H) | 421 (M + 1) | 0.1 |
| 3-amino-N-(5-(azetidin-3-ylmethoxy)isothiazol-4-yl)-6-(2,6-difluorophenyl)-5-fluoropicolinamide hydrochloride | 1H NMR (400 MHz, DMSO-d6) δ: 2.00-2.01 (m, 1H), 3.65-4.35 (m, 4H), 4.63 (d, J = 6, 2H), 7.20-7.30 (m, 2H), 7.34-7.36 (m,, 2H), 7.52-7.62 (m, 1H), 8.39 (dd, J = 8, 4 1H), 8.60 (s, 1H), 8.90 (bs, 2H), 10.24 (s, 1H) | 436 (M + 1) | 0.3 |
| 3-amino-N-(5-((1-amino-3-chloropropan-2-yl)oxy)isothiazol-4-yl)-6-(2,6-difluorophenyl)-5-fluoropicolinamide hydrochloride | 1H NMR (400 MHz, DMSO-d6) δ: 3.11 (dd, J = 12, 8, 1H), 3.22 (dd, J = 10, 4, 1H), 3.77 (d, J = 8, 2H), 4.20-4.30 (m, 1H), 7.20-7.30 (m, 2H), 7.30 (bs, 2H), 7.40 (t, J = 8, 2H), 7.45-7.75 (m, 1H), 7.99 (bs, 2H), 8.55 (dd, J = 8, 4, 1H), 9.20 (s, 1H), 10.05 (s, 1H) | 458 (M + 1) | 1.6 |
| 3-amino-N-(5-(3-amino-2-(chloromethyl)propoxy)isothiazol-4-yl)-6-(2,6-difluorophenyl)-5-fluoropicolinamide hydrochloride | 1H NMR (400 MHz, DMSO-d6) δ: 2.20-2.60 (m, 2H), 2.90-3.00 (m, 1H), 3.65 (s, 1H), 3.79 (d, J = 8, 2H), 4.20-4.38 (m, 2H), 7.20-7.30 (m, 2H), 7.30 (bs, 2H), 7.39 (t, J = 8, 2H), 7.45-7.75 (m, 1H), 8.12 (bs, 2H), 8.45 (dd, J = 8, 4, 1H), 8.90 (s, 1H), 9.90 (s, 1H) | 472 (M + 1) | 1.6 |
| 3-amino-6-(2,6-difluorophenyl)-5-fluoro-N-(5-(piperidin-3-ylmethoxy)isothiazol-4-yl)picolinamide hydrochloride | 1H NMR (400 MHz, DMSO-d6) δ: 1.40-1.50 (m, 1H), 1.66-1.80 (m, 1H), 2.03-2.08 (m, 1H), 2.20-2.28 (m, 1H), 2.54-2.60 (m, 1H), 2.70-2.76 (m, 2H), 3.10-3.50 (m, 2H), 4.20-4.40 (m, 2H), 7.20-7.30 (m, 2H), 7.30-7.36 (m, 2H), 7.50-7.62 (m, 1H), 8.40 (dd, J = 8, 4, 1H), 8.88 (s, 1H), 9.03 (bs, 2H), 10.35 (s, 1H) | 464 (M + 1) | 1.6 |
| 3-amino-N-(5-(4-aminobutoxy)isothiazol-4-yl)-6-(2,6-difluorophenyl)-5-fluoropicolinamide hydrochloride | 1H NMR (400 MHz, DMSO-d6) δ: 1.50-1.55 (m, 2H), 1.75-1.78 (m, 2H), 2.80-2.84 (m, 2H), 4.25 (t, J = 6, 2H), 7.21-7.31 (m, 2H), 7.34-7.36 (m, 3H), 7.50-7.60 (m, 1H), 7.90 (bs, 2H), 8.44 (dd, J = 8, 4, 1H), 7.75 (s, 1H), 10.25 (s, 1H) | 438 (M + 1) | 1.8 |
| 3-amino-N-(5-((3-aminocyclohexyl)oxy)isothiazol-4-yl)-6-(2,6-difluorophenyl)-5-fluoropicolinamide hydrochloride | 1H NMR (400 MHz, DMSO-d6) δ: 1.10-1.40 (m, 5H), 2.60-2.80 (m, 3H), 3.05-3.50 (m, 1H), 3.95-4.05 (H), 7.20-7.30 (m, 2H), 7.35-7.37 (m, 3H), 7.50-7.62 (m, 1H), 7.91 (bs, 3H), 8.42 (dd, J = 8, 4, 1H), 8.80-8.90 (m, 1H), 10.49 (s, 1H) | 464 (M + 1) | 2.9 |
| 3-amino-5-fluoro-6-phenyl-N-(5-(pyrrolidin-3-yloxy)isothiazol-4-yl)picolinamide hydrochloride | 1HNMR (400 MHz, DMSO-d6) δ: 2.10-2.15 (m, 1H), 2.28-2.30 (m, 1H), 2.98-3.02 (m, 1H), 3.28-3.30 (m, 1H), 3.30-3.35 (m, 2H), 5.60 (bs, 1H), 7.20-7.40 (m, 5H), 7.50-7.60 (m, 1H), 8.30-8.50 (m, 3H), 8.85 (s, 1H), 9.32 (bs, 2H), 10.05 (s, 1H) | 400 (M + 1) | 1.3 |
| 3-fluoro-N-(5-(piperidin-4-yloxy)isothiazol-4-yl)-[2,4'-bipyridine]-6-carboxamide hydrochloride | 1H NMR (400 MHz, DMSO-d6) δ: 1.80-2.00 (m, 2H), 2.16 (bs, 2H), 3.01 (bs, 2H), 3.20 (bs, 2H), 5.16 (bs, 1H), 7.20 (d, J = 8, 2H), 7.70-7.77 (m, 1H), 8.20 (t, J = 8, 1H), 8.40 (dd, J = 8, 4, 1H), 8.60 (s, 1H), 8.86 (bs, 1H), 9.20 (bs, 1H), 10.17 (s, 1H) | 400 (M + 1) | 0.3 |
| N-(5-(azepan-4-yloxy)isothiazol-4-yl)-6-(2,6-difluorophenyl)-3-fluoropicolinamide hydrochloride | 1H NMR (400 MHz, DMSO-d6) δ: 1.65-1.70 (m, 1H), 2.02-2.05 (m, 2H), 2.10-2.15 (m, 3H), 2.90-3.00 (m, 4H), 5.40-5.42 (m, 1H), 7.41 (t, J = 8, 2H), 7.69-7.75 (m, 1H), 8.26 (t, J = 8, 1H), 8.41 (dd, J = 8, 4, 1H), 8.58 (s, 1H), 8.75 (bs, 1H), 9.06 (bs, 1H), 10.14 (s, 1H) | 449 (M + 1) | 1.4 |
| N-(5-(azepan-4-yloxy)isothiazol-4-yl)-5-fluoro-6-(2-fluoro-6-methoxyphenyl)picolinamide hydrochloride | 1H NMR (400 MHz, DMSO-d6) δ: 1.65-1.70 (m, 1H), 2.06-2.08 (m, 2H), 2.08-2.12 (m, 3H), 2.90-3.00 (m, 4H), 3.81 (s, 3H), 5.40-5.42 (m, 1H), 7.20-7.30 (m, 2H), 7.70-7.75 (m, 1H), 8.25 (t, J = 8, 1H), 8.40 (dd, J = 8, 4, 1H), 8.61 (s, 1H), 8.65 (bs, 1H), 9.17 (bs, 1H), 10.16 (s, 1H) | 461 (M + 1) | 1.6 |
| N-(5-(azepan-4-yloxy)isothiazol-4-yl)-6-(2,6-difluorophenyl)-5-(trifluoromethyl)picolinamide hydrochloride | 1H NMR (400 MHz, DMSO-d6) δ: 1.65-1.68 (m, 1H), 2.00-2.05 (m, 2H), 2.10-2.15 (m, 3H), 2.90-3.00 (m, 4H), 5.41-5.44 (m, 1H), 7.44 (t, J = 8, 2H), 7.69-7.77 (m, 1H), 7.79 (d, J = 8 1H), 8.30 (d, J = 8, 1H), 8.60 (s, 1H), 9.08 (bs, 2H), 10.20 (s, 1H) | 499 (M + 1) | 0.4 |
| 6-(2,6-difluorophenyl)-N-(5-(piperidin-4-ylmethoxy)isothiazol-4-yl)-5-(trifluoromethyl)picolinamide hydrochloride | 1H NMR (400 MHz, DMSO-d6) δ: 1.99 (bs, 2H), 2.00-2.10 (m, 2H), 2.70-2.90 (m, 2H), 2.90-3.70 (m, 5H), 4.30 (bs, 2H), 7.40 (t, J = 8, 2H), 7.69-7.75 (m, 1H), 7.80 (d, J = 8, 1H), 8.31 (d, J = 8, 1H), 8.60 (s, 1H), 9.08 (bs, 2H), 10.21 (s, 1H) | 499 (M + 1) | 0.3 |
| N-(5-(azetidin-3-ylmethoxy)isothiazol-4-yl)-6-(2,6-difluorophenyl)-5-(trifluoromethyl)picolinamide hydrochloride | 1H NMR (400 MHz, DMSO-d6) δ: 1.98-2.02 (m, 1H), 3.60-4.40 (m, 4H), 4.64 (d, J = 6, 2H), 7.42 (t, J = 8, 2H), 7.68-7.75 (m, 1H), 7.83 (d, J = 8, 1H), 8.29 (d, J = 8, 1H), 8.65 (s, 1H), 9.20 (bs, 2H), 10.13 (s, 1H) | 471 (M + 1) | 0.3 |

TABLE I-continued

Analytical and CFTR activity data of the compounds described in the examples of the present invention

| Name | NMR | MS | CFTR Activity |
|---|---|---|---|
| 6-(2,6-difluorophenyl)-N-(5-(piperidin-4-yloxy)isothiazol-4-yl)-5-(trifluoromethyl)picolinamide hydrochloride | 1H NMR (400 MHz, DMSO-d6) δ: 1.80-2.00 (m, 2H), 2.20 (bs, 2H), 3.00 (bs, 2H), 3.22 (bs, 2H), 5.12 (bs, 1H), 7.43 (t, J = 8, 2H), 7.70-7.75 (m, 1H), 7.79 (d, J = 8, 1H), 8.28 (d, J = 8, 1H), 8.65 (s, 1H), 9.01 (bs, 2H), 10.15 (s, 1H) | 485 (M + 1) | 1.7 |
| N-(5-(((1r,4r)-4-aminocyclohexyl)oxy)isothiazol-4-yl)-6-(2,6-difluorophenyl)-5-(trifluoromethyl)picolinamide hydrochloride | 1H NMR (400 MHz, DMSO) δ: 1.15-1.50 (m, 2H), 1.65-1.70 (m, 2H), 1.98-2.02 (m, 2H), 2.20-2.25 (m, 2H), 2.85-2.90 (m, 1H), 5.33-5.40 (m, 1H), 7.39 (t, J = 8, 2H), 7.70-7.75 (m, 1H), 7.77 (d, J = 8, 1H), 8.30 (d, J = 8, 1H), 8.60 (s, 1H), 9.08 (bs, 2H), 10.18 (s, 1H) | 499 (M + 1) | 1 |
| 6-(2,6-difluorophenyl)-N-(5-((tetrahydro-2H-pyran-4-yl)methoxy)isothiazol-4-yl)-5-(trifluoromethyl)picolinamide | 1H NMR (400 MHz, DMSO-d6) δ: 1.70-1.80 (m, 1H), 2.20-2.35 (m, 2H), 2.60-2.68 (m, 2H), 3.70-3.80 (m, 2H), 4.00-4.05 (m, 4H), 7.42 (t, J = 8, 2H), 7.69-7.75 (m, 1H), 7.80 (d, J = 8, 1H), 8.29 (d, J = 8, 1H), 8.70 (s, 1H), 9.13 (bs, 2H), 10.27 (s, 1H) | 500 (M + 1) | 0.6 |
| 3-amino-N-(5-(azepan-4-yloxy)isothiazol-4-yl)-6-(2,6-difluorophenyl)-5-(trifluoromethyl)picolinamide hydrochloride | 1H NMR (400 MHz, DMSO-d6) δ: 1.70 (s, 1H), 2.05-2.08 (m, 2H), 2.10-2.15 (m, 3H), 2.90-3.00 (m, 4H), 5.40-5.44 (m, 1H), 7.39 (bs, 2H), 7.42 (t, J = 8, 2H), 7.71-7.75 (m, 1H), 7.78 (s, 1H), 8.63 (s, 1H), 8.91 (bs, 2H), 10.15 (s, 1H) | 514 (M + 1) | 0.7 |
| 3-amino-6-(2,6-difluorophenyl)-N-(5-(piperidin-4-ylmethoxy)isothiazol-4-yl)-5-(trifluoromethyl)picolinamide hydrochloride | 1H NMR (400 MHz, DMSO-d6) δ 1.67-1.80 (m, 1H), 2.20-2.35 (m, 2H), 2.60-2.70 (m, 2H), 3.75-3.85 (m, 2H), 4.00-4.05 (m, 4H), 7.38 (bs, 2H), 7.44 (t, J = 8, 2H), 7.70-7.75 (m, 1H), 7.78 (s, 1H), 8.60 (s, 1H), 9.09 (bs, 2H), 10.17 (s, 1H) | 514 (M + 1) | 0.2 |
| 3-amino-N-(5-(azetidin-3-ylmethoxy)isothiazol-4-yl)-6-(2,6-difluorophenyl)-5-(trifluoromethyl)picolinamide hydrochloride | 1HNMR (400 MHz, DMSO-d6) δ: 1.99-2.02 (m, 1H), 3.60-4.40 (m, 4H), 4.60 (d, J = 6, 2H), 7.40 (bs, 2H), 7.43 (t, J = 8, 2H), 7.70-7.75 (m, 1H), 7.79 (s, 1H), 8.64 (s, 1H), 9.12 (bs, 2H), 10.23 (s, 1H) | 486 (M + 1) | 0.1 |
| 3-amino-6-(2,6-difluorophenyl)-N-(5-(piperidin-4-yloxy)isothiazol-4-yl)-5-(trifluoromethyl)picolinamide hydrochloride | 1H NMR (400 MHz, DMSO-d6) δ: 1.70-1.90 (m, 2H), 2.20 (bs, 2H), 3.02 (bs, 2H), 3.20 (bs, 2H), 5.11 (bs, 1H), 7.39 (bs, 2H), 7.43 (t, J = 8, 2H), 7.70-7.76 (m, 1H), 7.79 (s, 1H), 8.61 (s, 1H), 9.19 (bs, 2H), 10.14 (s, 1H) | 500 (M + 1) | 0.7 |
| 3-amino-N-(5-(((1r,4r)-4-aminocyclohexyl)oxy)isothiazol-4-yl)-6-(2,6-difluorophenyl)-5-(trifluoromethyl)picolinamide hydrochloride | 1H NMR (400 MHz, DMSO-d6) δ: 1.15-1.30 (m, 2H), 1.45-1.55 (m, 2H), 1.80-1.90 (m, 2H), 2.05-2.15 (m, 2H), 3.10 (bs, 1H), 4.90 (bs, 1H), 7.39 (bs, 2H), 7.45 (t, J = 8, 2H), 7.69-7.76 (m, 1H), 7.79 (s, 1H), 8.61 (s, 1H), 8.97 (bs, 2H), 10.13 (s, 1H) | 514 (M + 1) | 4.6 |
| 3-amino-6-phenyl-N-(5-(pyrrolidin-3-yloxy)isothiazol-4-yl)-5-(trifluoromethyl)picolinamide hydrochloride | 1H NMR (400 MHz, DMSO-d6) δ: 2.00-2.20 (m, 1H), 2.28-2.30 (m, 1H), 3.00-3.02 (m, 1H), 3.25-3.30 (m, 1H), 3.30-3.34 (m, 2H), 5.72 (bs, 1H), 7.39 (bs, 2H), 7.42 (t, J = 8, 2H), 7.70-7.75 (m, 1H), 7.78 (s, 1H), 8.60 (s, 1H), 9.01 (bs, 1H), 9.19 (s, 1H), 10.07 (s, 1H) | 450 (M + 1) | 0.4 |
| N-(5-(3-amino-2-(chloromethyl)propoxy)isothiazol-4-yl)-6-(2,6-difluorophenyl)-5-(trifluoromethyl)picolinamide hydrochloride | 1H NMR (400 MHz, DMSO-d6) δ: 2.20-2.55 (m, 1H), 2.90-3.05 (m, 2H), 3.65 (s, 1H), 3.81 (d, J = 8, 2H), 4.20-4.40 (m, 2H), 7.41 (t, J = 8, 2H), 7.70-7.75 (m, 1H), 7.77 (d, J = 8, 1H), 8.30 (d, J = 8, 1H), 8.72 (s, 1H), 9.18 (bs, 2H), 10.21 (s, 1H) | 507 (M + 1) | 0.5 |
| 3-amino-N-(5-(3-amino-2-(chloromethyl)propoxy)isothiazol-4-yl)-6-(2,6-difluorophenyl)-5-(trifluoromethyl)picolinamide hydrochloride | 1HNMR (400 MHz, DMSO-d6) δ: 2.20-2.70 (m, 1H), 2.90-3.00 (m, 2H), 3.60 (s, 1H), 3.82 (d, J = 8, 2H), 4.20-4.40 (m, 2H), 7.39 (bs, 2H), 7.42 (t, J = 8, 2H), 7.70-7.75 (m, 1H), 7.79 (s, 1H), 8.58 (s, 1H), 9.02 (bs, 2H), 10.15 (s, 1H) | 522 (M4 + 1) | 0.5 |
| N-(5-(3-amino-2-(hydroxymethyl)propoxy)isothiazol-4-yl)-6-(2,6-difluorophenyl)-5-fluoropicolinamide hydrochloride | 1H NMR (400 MHz, DMSO-d6) δ: 2.30-2.70 (m, 1H), 2.90-3.00 (m, 2H), 3.65 (s, 1H), 3.68-3.70 (m, 2H), 3.79 (d, J = 8, 2H), 4.59 (s, 1H), 7.42 (t, 8, 2H), 7.68-7.75 (m, 1H), 8.20 (t, J = 8, 1H), 8.40 (dd, J = 8, 4, 1H), 8.62 (s, 1H), 10.07 (s, 1H) | 439 (M + 1) | 0.5 |
| 3-amino-N-(5-(3-amino-2-(hydroxymethyl)propoxy)isothiazol-4-yl)-6-(2,6-difluorophenyl)-5-fluoropicolinamide hydrochloride | 1HNMR (400 MHz, DMSO-d6) δ: 2.20-2.70 (m, 1H), 2.90-3.00 (m, 2H), 3.62 (s, 1H), 3.70-3.75 (m, 2H), 3.80 (d, J = 8, 2H), 4.55 (s, 1H), 7.20-7.30 (m, 3H), 7.35 (d, J = 8, 1H), 7.37 (bs, 2H), 7.50-7.60 (m, 1H), 8.41 (dd, J = 8, 4, 1H), 8.80 (s, 1H), 9.19 (bs, 2H), 10.10 (s, 1H) | 454 (M + 1) | 1.8 |
| N-(5-(3-amino-2-(hydroxymethyl)propoxy)isothiazol-4-yl)-6-(2,6-difluorophenyl)-5-(trifluoromethyl)picolinamide hydrochloride | 1H NMR (400 MHz, DMSO-d6) δ: 2.20-2.60 (m, 1H), 2.90-3.05 (m, 2H), 3.66 (s, 1H), 3.65-3.70 (m, 2H), 3.81 (d, J = 8, 2H), 4.60 (s, 1H), 7.40 (t, J = 8, 2H), 7.70-7.75 (m, 1H), 7.77 (d, J = 8, 1H), 8.30 (d, J = 8, 1H), 8.62 (s, 1H), 9.18 (bs, 2H), 10.16 (s, 1H) | 489 (M + 1) | 2 |
| 3-amino-N-(5-(3-amino-2-(hydroxymethyl)propoxy)isothiazol-4-yl)-6-(2,6-difluorophenyl)-5-(trifluoromethyl)picolinamide hydrochloride | 1HNMR (400 MHz, DMSO-d6) δ: 2.20-2.70 (m, 1H), 2.90-3.00 (m, 2H), 3.62 (s, 1H), 3.65-3.70 (m, 2H), 3.81 (d, J = 8, 2H), 4.61 (s, 1H), 7.39 (bs, 2H), 7.40 (t, J = 8, 2H), 7.70-7.75 (m, 1H), 7.80 (s, 1H), 8.60 (s, 1H), 9.09 (bs, 2H), 10.15 (s, 1H) | 504 (M + 1) | 2.3 |

TABLE I-continued

Analytical and CFTR activity data of the compounds described in the examples of the present invention

| Name | NMR | MS | CFTR Activity |
|---|---|---|---|
| N-(5-((3-aminocyclohexyl)oxy)isothiazol-4-yl)-6-(2,6-difluorophenyl)-5-(trifluoromethyl)picolinamide hydrochloride | 1H NMR (400 MHz, DMSO-d6) δ: 1.10-1.45 (m, 5H), 2.65-2.80 (m, 3H), 3.00-3.50 (m, 1H), 3.95-4.05 (m, 0.7H), 4.40 (bs, 0.3H), 7.41 (t, J = 8, 2H), 7.70-7.75 (m, 1H), 7.75 (d, J = 8, 1H), 8.32 (d, J = 8, 1H), 8.60 (s, 1H), 9.17 (bs, 2H), 10.25 (s, 1H) | 499 (M + 1) | 0.1 |
| 3-amino-N-(5-((3-aminocyclohexyl)oxy)isothiazol-4-yl)-6-(2,6-difluorophenyl)-5-(trifluoromethyl)picolinamide hydrochloride | 1HNMR (400 MHz, DMSO-d6) δ: 1.15-1.40 (m, 5H), 2.60-2.80 (m, 3H), 3.05-3.55 (m, 1H), 4.00-4.05 (m, 0.7H), 4.45 (bs, 0.3H), 7.39 (bs, 2H), 7.40 (t, J = 8, 2H), 7.70-7.75 (m, 1H), 7.80 (s, 1H), 8.60 (s, 1H), 9.09 (bs, 2H), 10.15 (s, 1H) | 514 (M + 1) | 0.4 |

We claim:

1. A compound having a structure of Formula II, or a stereoisomer, a tautomer, or a pharmaceutically acceptable salt thereof:

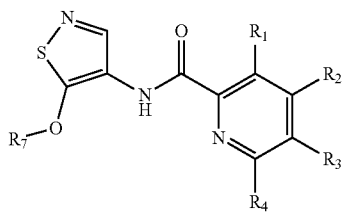

II wherein $R_1$ is a hydrogen, —$NHR_5$, a halogen, a hydroxyl, an alkyl having 1 to 5 carbon atoms, a cyano, or a nitro;

$R_2$ is a hydrogen, a halogen, a hydroxyl, an alkyl having 1 to 5 carbon atoms, an amino, a cyano, or a nitro group;

$R_3$ is a halogen, a hydroxyl, a halogenated alkyl having 1 to 5 carbon atoms, an alkoxyl being optionally substituted with a halogen, an amino, a cyano, or a nitro group;

$R_4$ is a 4 to 8 membered optionally substituted aryl, heteroaryl, cycloalkyl, or heterocyclyl, and the hetero atom on the heteroaryl or heterocyclyl is a nitrogen, an oxygen, or a sulfur; $R_4$ is optionally substituted by one or more group that is a halogen, a hydroxyl, a cyano, an amino, a $C_{1-4}$ alkylamine, a $C_{1-4}$ alkyl, a $C_{3-6}$ cycloalkyl, a $C_{1-4}$ alkoxyl, a nitro, a carboxy, a carbonyl, or a $C_{1-4}$ carboalkoxy;

$R_5$ is a hydrogen or an alkyl having 1 to 5 carbon atoms;

$R_7$ is an alkyl having 1 to 8 carbon atoms and being optionally substituted by an amino, a hydroxyl, a halogen, a methyl, an ethyl, a halogenated methyl, or a halogenated ethyl, or a group having a formula:

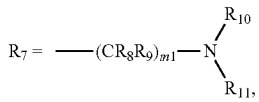

or a group having a formula:

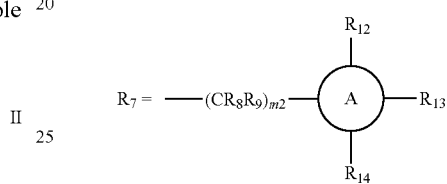

Wherein each of $R_8$ and $R_9$ is a hydrogen, a halogen, or a hydroxyl;

each of $R_{10}$ and $R_{11}$ is independently selected from a hydrogen or an alkyl having 1 to 3 carbon atoms, and m1 is 2, 3, 4, or 5, m2 is 0, 1, or 2, Ring A is a 4 to 8 membered optionally substituted aryl, heteroaryl, or cycloalkyl, and the heteroaryl has 1 or 2 hetero atoms that are independently selected from an oxygen, a nitrogen, or a sulfur, and each of $R_{12}$, $R_{13}$, $R_{14}$ is independently selected from a hydrogen, a halogen, a hydroxyl group, an amino, or an alkyl group having 1 to 5 carbon atoms.

2. The compound according to claim 1, wherein $R_7$ is a substituted or unsubstituted cyclobutyl, cyclopentyl, cyclohexyl, cycloheptyl, azetidyl, pyrrolidinyl, piperidinyl, azepanyl, oxetyl, tetrahydrofuryl, or tetrahydropyranyl, and the cyclic group on $R_7$ is optionally substituted with up to three substituents, and each of the substitutent is an amino, a hydroxy, or a methyl;

$R_1$ is a hydrogen, an amino, or a fluoro;

$R_2$ is a hydrogen, a halogen, or a methyl;

$R_3$ is a halogen, a hydroxyl, a halogenated $C_{1-3}$ alkyl, an alkoxyl having 1 to 3 carbon atoms and being optionally substituted with a halogen, an amino, a cyano, or a nitro group; and $R_4$ is a substituted or unsubstituted phenyl, wherein the substituted phenyl group is substituted with up to three substituents that is a cyano, a nitro, a halogen, a hydroxyl, an amino, a $C_{1-4}$ alkylamine, an alkyl having 1 to 4 carbon atoms, or a cycloalkyl having 3 to 6 carbon atoms.

3. The compound according to claim 2, wherein $R_7$ is a substituted or unsubstituted cyclohexyl, cycloheptyl, pyrrolidinyl, piperidinyl, or azepanyl group;

when the cyclic group on $R_7$ group is substituted, it has up to three substitutents that is an amino, a hydroxy, or a methyl;

$R_1$ is a hydrogen, an amino, or a fluoro;

$R_2$ is a hydrogen, a halogen, or a methyl;

$R_3$ is a halogen, a methoxyl, a $CF_3$, or a OCF3; and

R₄ is a substituted or unsubstituted phenyl, and the substituted phenyl group is substituted with up to three substitutents that is a cyano, a nitro group, a halogen, or a hydroxyl.

4. The compound according to claim 3, wherein $R_1$ is a hydrogen or an amino; $R_2$ is hydrogen; $R_3$ is a halogen; $R_4$ is a substituted or unsubstituted phenyl, and the substituted phenyl is substituted with up to three substituents that is a halogen.

5. The compound according to claim 1, wherein $R_7$ is a substituted or unsubstituted cyclobutylmethyl, cyclopentylmethyl, cyclohexylmethyl, cycloheptylmethyl, azetidylmethyl, pyrrolidinylmethyl, piperidinylmethyl, azepanylmethyl, oxetylmethyl, tetrahydrofurylmethyl, or tetrahydropyranylmethyl group;
  when the cyclic group on $R_7$ group is substituted, it has up to three substitutents that is an amino, a hydroxy, or a methyl;
  $R_1$ is a hydrogen, an amino, or a fluoro;
  $R_2$ is a hydrogen, a halogen, or a methyl;
  $R_3$ is a halogen, a hydroxyl, a halogenated $C_{1-3}$ alkyl, alkoxyl having 1 to 3 carbon atoms and being optionally substituted with a halogen, an amino, a cyano, or a nitro group; and
  $R_4$ is a substituted or unsubstituted phenyl, wherein the substituted phenyl group is substituted with up to three substitutents that is a cyano, a nitro, a halogen, a hydroxyl, an amino, a $C_{1-4}$ alkylamine, an alkyl having 1 to 4 carbon atoms, or a cycloalkyl having 3 to 6 carbon atoms.

6. The compound according to claim 5, wherein $R_7$ is a substituted or unsubstituted cyclohexylmethyl, cycloheptyl, pyrrolidinylmethyl, piperidinylmethyl, or azepanylmethyl group,
  when the cyclic group on $R_7$ is substituted, it has up to three substitutents that is an amino, a hydroxy, or a methyl;
  $R_1$ is a hydrogen, an amino, or a fluoro;
  $R_2$ is a hydrogen, a halogen, or a methyl;
  $R_3$ is a halogen, a methoxyl, a $CF_3$, or an OCF3; and
  $R_4$ is a substituted or unsubstituted phenyl, and the substituted phenyl group is substituted with up to three substitutents that is a cyano, a nitro group, a halogen, or a hydroxyl.

7. The compound according to claim 6, wherein $R_1$ is a hydrogen or an amino;
  $R_2$ is hydrogen;
  $R_3$ is a halogen; and
  $R_6$ is a substituted or unsubstituted phenyl, and the substituted phenyl is substituted with up to three substituents that is a halogen.

8. The compound according to claim 1, wherein $R_7$ is a substituted $C_{2-5}$ alkyl,
  the substituted $R_7$ group is substituted at any position with up to four substitutents that is an amino, a halogen, a methyl, an ethyl, a halogenated methyl, or a halogenated ethyl;
  $R_1$ is a hydrogen or an amino;
  $R_2$ is a hydrogen;
  $R_3$ is a halogen; and
  $R_4$ is a substituted or unsubstituted phenyl, and the substituted phenyl is substituted with up to three substituents that is a halogen.

9. A CFTR modulator, wherein the CFTR modulator is a compound that is 6-(2,6-difluorophenyl)-5-fluoro-N-(5-(piperidin-4-ylmethoxy)isothiazol-4-yl)picolinamide hydrochloride, N-(5-(azetidin-3-ylmethoxy)isothiazol-4-yl)-6-(2,6-difluorophenyl)-5-fluoropicolinamide hydrochloride, 6-(2,6-difluorophenyl)-5-fluoro-N-(5-(piperidin-4-yloxy)isothiazol-4-yl)picolinamide hydrochloride, 6-(2,6-difluorophenyl)-5-fluoro-N-(5-(pyrrolidin-3-yloxy)isothiazol-4-yl)picolinamide hydrochloride, 6-(2,6-difluorophenyl)-5-fluoro-N-(5-(piperidin-3-yloxy)isothiazol-4-yl)picolinamide hydrochloride, N-(5-(azepan-4-yloxy)isothiazol-4-yl)-6-(2,6-difluorophenyl)-5-fluoropicolinamide hydrochloride, 6-(2,6-difluorophenyl)-5-fluoro-N-(5-(piperidin-3-ylmethoxy)isothiazol-4-yl)picolinamide hydrochloride, 6-(2,6-difluorophenyl)-5-fluoro-N-(5-(pyrrolidin-3-ylmethoxy)isothiazol-4-yl)picolinamide hydrochloride, N-(5-(azetidin-3-yloxy)isothiazol-4-yl)-6-(2,6-difluorophenyl)-5-fluoropicolinamide hydrochloride, N-(5-(((1r,4r)-4-aminocyclohexyl)oxy)isothiazol-4-yl)-6-(2,6-difluorophenyl)-5-fluoropicolinamide hydrochloride, N-(5-((3-aminocyclohexyl)oxy)isothiazol-4-yl)-6-(2,6-difluorophenyl)-5-fluoropicolinamide hydrochloride, N-(5-(3-aminopropoxy)isothiazol-4-yl)-6-(2,6-difluorophenyl)-5-fluoropicolinamide hydrochloride, 6-(2,6-difluorophenyl)-5-fluoro-N-(5-(3-(methylamino)propoxy)isothiazol-4-yl)picolinamide hydrochloride, 6-(2,6-difluorophenyl)-N-(5-(3-(dimethylamino)propoxy)isothiazol-4-yl)-5-fluoropicolinamide hydrochloride, N-(5-(4-aminobutoxy)isothiazol-4-yl)-6-(2,6-difluorophenyl)-5-fluoropicolinamide hydrochloride, 6-(2,6-difluorophenyl)-5-fluoro-N-(5-(4-(methylamino)butoxy)isothiazol-4-yl)picolinamide hydrochloride, 6-(2,6-difluorophenyl)-5-fluoro-N-(5-(3-hydroxypropoxy)isothiazol-4-yl)picolinamide, 6-(2,6-difluorophenyl)-5-fluoro-N-(5-(3-hydroxybutoxy)isothiazol-4-yl)picolinamide, 6-(2,6-difluorophenyl)-5-fluoro-N-(5-(4-hydroxybutoxy)isothiazol-4-yl)picolinamide, 6-(2,6-difluorophenyl)-5-fluoro-N-(5-((4-hydroxy-4-methylpentyl)oxy)isothiazol-4-yl)picolinamide, 6-(2,6-difluorophenyl)-N-(5-(3,4-dihydroxybutoxy)isothiazol-4-yl)-5-fluoropicolinamide, 6-(2,6-difluorophenyl)-5-fluoro-N-(5-((tetrahydro-2H-pyran-4-yl)methoxy)isothiazol-4-yl)picolinamide, 3-amino-6-(2,6-difluorophenyl)-5-fluoro-N-(5-(piperidin-4-ylmethoxy)isothiazol-4-yl)picolinamide hydrochloride, 3-amino-6-(2,6-difluorophenyl)-5-fluoro-N-(5-(pyrrolidin-3-yloxy)isothiazol-4-yl)picolinamide hydrochloride, 3-amino-6-(2,6-difluorophenyl)-5-fluoro-N-(5-(piperidin-4-yloxy)isothiazol-4-yl)picolinamide hydrochloride, 3-amino-N-(5-(azepan-4-yloxy)isothiazol-4-yl)-6-(2,6-difluorophenyl)-5-fluoropicolinamide hydrochloride, 3-amino-N-(5-(((1r,4r)-4-aminocyclohexyl)oxy)isothiazol-4-yl)-6-(2,6-difluorophenyl)-5-fluoropicolinamide hydrochloride, 3-amino-6-(2,6-difluorophenyl)-5-fluoro-N-(5-(pyrrolidin-3-ylmethoxy)isothiazol-4-yl)picolinamide hydrochloride, N-(5-((1-amino-3-chloropropan-2-yl)oxy)isothiazol-4-yl)-6-(2,6-difluorophenyl)-5-fluoropicolinamide hydrochloride, N-(5-(3-amino-2-(chloromethyl)propoxy)isothiazol-4-yl)-6-(2,6-difluorophenyl)-5-fluoropicolinamide hydrochloride, 3-amino-N-(5-(azetidin-3-yloxy)isothiazol-4-yl)-6-(2,6-difluorophenyl)-5-fluoropicolinamide hydrochloride, 3-amino-N-(5-(azetidin-3-ylmethoxy)isothiazol-4-yl)-6-(2,6-difluorophenyl)-5-fluoropicolinamide hydrochloride, 3-amino-N-(5-((1-amino-3-chloropropan-2-yl)oxy)isothiazol-4-yl)-6-(2,6-difluorophenyl)-5-fluoropicolinamide hydrochloride, 3-amino-N-(5-(3-amino-2-(chloromethyl)propoxy)isothiazol-4-yl)-6-(2,6-difluorophenyl)-5-fluoropicolinamide hydrochloride, 3-amino-6-(2,6-difluorophenyl)-5-fluoro-N-(5-(piperidin-3-ylmethoxy)isothiazol-4-yl)picolinamide hydrochloride, 3-amino-N-(5-(4-aminobutoxy)isothiazol-4-yl)-6-(2,6-difluorophenyl)-5-fluoropicolinamide hydrochloride, 3-amino-N-(5-((3-aminocyclohexyl)oxy)isothiazol-4-yl)-6-(2,6-difluorophenyl)-5-fluoropicolinamide hydrochloride, 3-amino-5-fluoro-6-phenyl-N-(5-(pyrrolidin-3-yloxy)isothiazol-4-yl)picolinamide hydrochloride, 3-fluoro-N-(5-(piperidin-4-yloxy)isothiazol-4-yl)-[2,4'-bipyridine]-6-carboxamide hydrochloride, N-(5-(azepan-4-yloxy)isothiazol-4-yl)-6-(2,6-difluorophenyl)-3-fluoropicolinamide hydrochloride, N-(5-(azepan-4-yloxy)isothiazol-4-yl)-5-fluoro-6-(2-fluoro-6-methoxyphenyl)picolinamide hydrochloride, N-(5-(azepan-4-yloxy)isothiazol-4-yl)-6-(2,6-difluorophenyl)-5-(trifluoromethyl)picolinamide hydrochloride, 6-(2,6-difluorophenyl)-N-(5-(piperidin-4-ylmethoxy)isothiazol-4-yl)-5-(trifluoromethyl)picolinamide hydrochloride, N-(5-(azetidin-3-ylmethoxy)isothiazol-4-yl)-6-(2,6-difluorophenyl)-5-(trifluoromethyl)picolinamide hydrochloride, 6-(2,6-difluorophenyl)-N-(5-(piperidin-4-yloxy)isothiazol-4-yl)-5-(trifluoromethyl)picolinamide hydrochloride, N-(5-(((1r,4r)-4-aminocyclohexyl)oxy)isothiazol-4-yl)-6-(2,6-difluorophenyl)-5-(trifluoromethyl)picolinamide hydrochloride, 6-(2,6-difluorophenyl)-N-(5-(((tetrahydro-2H-pyran-4-yl)methoxy)isothiazol-4-yl)-5-(trifluoromethyl)picolinamide, 3-amino-N-(5-(azepan-4-yloxy)isothiazol-4-yl)-6-(2,6-difluorophenyl)-5-(trifluoromethyl)picolinamide hydrochloride, 3-amino-6-(2,6-difluorophenyl)-N-(5-(piperidin-4-ylmethoxy)isothiazol-4-yl)-5-(trifluoromethyl)picolinamide hydrochloride, 3-amino-N-(5-(azetidin-3-ylmethoxy)isothiazol-4-yl)-6-(2,6-difluorophenyl)-5-(trifluoromethyl)picolinamide hydrochloride, 3-amino-6-(2,6-difluorophenyl)-N-(5-(piperidin-4-yloxy)isothiazol-4-yl)-5-(trifluoromethyl)picolinamide hydrochloride, 3-amino-N-(5-(((1r,4r)-4-aminocyclohexyl)oxy)isothiazol-4-yl)-6-(2,6-difluorophenyl)-5-(trifluoromethyl)picolinamide hydrochloride, 3-amino-6-phenyl-N-(5-(pyrrolidin-3-yloxy)isothiazol-4-yl)-5-(trifluoromethyl)picolinamide hydrochloride, N-(5-(3-amino-2-(chloromethyl)propoxy)isothiazol-4-yl)-6-(2,6-difluorophenyl)-5-(trifluoromethyl)picolinamide hydrochloride, 3-amino-N-(5-(3-amino-2-(chloromethyl)propoxy)isothiazol-4-yl)-6-(2,6-difluorophenyl)-5-(trifluoromethyl)picolinamide hydrochloride, N-(5-(3-amino-2-(hydroxymethyl)propoxy)isothiazol-4-yl)-6-(2,6-difluorophenyl)-5-fluoropicolinamide hydrochloride, 3-amino-N-(5-(3-amino-2-(hydroxymethyl)propoxy)isothiazol-4-yl)-6-(2,6-difluorophenyl)-5-fluoropicolinamide hydrochloride, N-(5-(3-amino-2-(hydroxymethyl)propoxy)isothiazol-4-yl)-6-(2,6-difluorophenyl)-5-(trifluoromethyl)picolinamide hydrochloride, 3-amino-N-(5-(3-amino-2-(hydroxymethyl)propoxy)isothiazol-4-yl)-6-(2,6-difluorophenyl)-5-(trifluoromethyl)picolinamide hydrochloride, N-(5-((3-aminocyclohexyl)oxy)isothiazol-4-yl)-6-(2,6-difluorophenyl)-5-(trifluoromethyl)picolinamide hydrochloride, or 3-amino-N-(5-((3-aminocyclohexyl)oxy)isothiazol-4-yl)-6-(2,6-difluorophenyl)-5-(trifluoromethyl)picolinamide hydrochloride.

10. A method for treating a subject having a disease caused by loss of cystic fibrosis transmembrane conductance regulator protein-mediated ion transport according to claim 1, comprising
   administering to the subject a therapeutically effective amount of the compound as described in claim 1,
   wherein the disease is cystic fibrosis in lungs, pancreas, gastrointestinal system, sinuses, reproductive system, and sweat glands.

11. A method for treating a subject having a disease caused by loss of cystic fibrosis transmembrane conductance regulator protein-mediated ion transport according to claim 9, comprising
   administering to the subject a therapeutically effective amount of the compound as described in claim 9,
   wherein the disease is cystic fibrosis in lungs, pancreas, gastrointestinal system, sinuses, reproductive system, and sweat glands.

12. A pharmaceutical composition according to claim 1, comprising the compound of claim 1 as an active pharmaceutical ingredient, and pharmaceutically acceptable carriers and adjuvants.

13. A pharmaceutical composition according to claim 9, comprising the compound of claim 9 as an active pharmaceutical ingredient, and pharmaceutically acceptable carriers and adjuvants.

14. The pharmaceutical composition according to claim 12, further comprising
   antibiotics, antihistamines, anti-inflammatory agents, bronchodilatory agents, epithelial sodium channel blockers, osmotic agents, or a combination thereof.

15. The pharmaceutical composition according to claim 13, further comprising
   antibiotics, antihistamines, anti-inflammatory agents, bronchodilatory agents, epithelial sodium channel blockers, osmotic agents, or a combination thereof.

* * * * *